United States Patent

Cochran et al.

(10) Patent No.: US 6,762,179 B2
(45) Date of Patent: Jul. 13, 2004

(54) THIAZOLE COMPOUNDS USEFUL AS INHIBITORS OF PROTEIN KINASE

(75) Inventors: John Cochran, Marshfield, MA (US); Suganthini Nanthakumar, Newton, MA (US); Edmund Harrington, South Boston, MA (US); Jian Wang, Boston, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 57 days.

(21) Appl. No.: 10/154,118

(22) Filed: May 23, 2002

(65) Prior Publication Data

US 2003/0119856 A1 Jun. 26, 2003

Related U.S. Application Data

(60) Provisional application No. 60/295,158, filed on Jun. 1, 2001.

(51) Int. Cl.[7] ..................... A61K 31/505; C07D 239/28
(52) U.S. Cl. ................... 514/227.8; 544/330; 544/331; 544/332; 544/122; 544/60; 514/231.5; 514/252.14; 514/275
(58) Field of Search ............................... 544/330, 331, 544/332; 514/275, 60, 122, 227.8, 231.5, 252.14

(56) References Cited

U.S. PATENT DOCUMENTS 5,958,935 A    9/1999   Davis et al. ................ 514/275

FOREIGN PATENT DOCUMENTS

WO    WO 00/78731    12/2000

OTHER PUBLICATIONS

Chalmers (TiPS vol 17, pp. 166–172 Apr. 1996).*
Philip Cohen and Sheelagh Frame (Nature Reviews/Molecular Cell Biology, vol. 2, pp. 769–776, Oct. 2001).*

* cited by examiner

Primary Examiner—Richard L. Raymond
Assistant Examiner—Kahsay Habte
(74) Attorney, Agent, or Firm—Andrea L. C. Rodidoux; Vertex Pharmaceuticals Incorporated

(57) ABSTRACT

The present invention provides a compound of formula I:

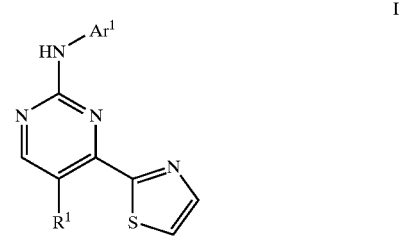

or a pharmaceutically acceptable derivative thereof, wherein $Ar^1$ is phenyl and $R^1$ is as defined in the specification. These compounds are inhibitors of protein kinases, particularly inhibitors of GSK3, Aurora2, and Syk mammalian protein kinases. The invention also provides pharmaceutically acceptable compositions comprising the compounds of the invention and methods of utilizing those compounds and compositions in the treatment of various protein kinase mediated disorders.

11 Claims, No Drawings

THIAZOLE COMPOUNDS USEFUL AS INHIBITORS OF PROTEIN KINASE

CROSS REFERENCE TO RELATED APPLICATION

This application claims priority to U.S. Provisional Patent Application 60/295,158 filed Jun. 1, 2001, the contents of which are incorporated herein by reference.

FIELD OF THE INVENTION

The present invention relates to compounds that are protein kinase inhibitors, pharmaceutically acceptable compositions comprising said compounds, and methods of use thereof. More particularly, the compounds are inhibitors of GSK-3, Aurora2, and Syk protein kinases and are useful for treating, or lessening the severity of, a variety of diseases and conditions, such as diabetes, Alzheimer's disease, stroke, proliferative disorders, and asthma.

BACKGROUND OF THE INVENTION

The search for new therapeutic agents has been greatly aided in recent years by better understanding of the structure of enzymes and other biomolecules associated with target diseases. One important class of enzymes that has been the subject of extensive study is the protein kinases.

Protein kinases mediate intracellular signal transduction. They do this by affecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g. osmotic shock, heat shock, ultraviolet radiation, bacterial endotoxin, $H_2O_2$), cytokines (e.g. interleukin-1 (IL-1) and tumor necrosis factor $\alpha$ (TNF-$\alpha$)), and growth factors (e.g. granulocyte macrophage-colony-stimulating factor (GM-CSF), and fibroblast growth factor (FGF). An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases and conditions are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Glycogen synthase kinase-3 (GSK-3) is a serine/threonine protein kinase comprised of $\alpha$ and $\beta$ isoforms that are each encoded by distinct genes [Coghlan et al., *Chemistry & Biology*, 7, 793–803 (2000); Kim and Kimmel, *Curr. Opinion Genetics Dev.*, 10, 508–514 (2000)]. GSK-3 has been implicated in various diseases including diabetes, Alzheimer's disease, CNS disorders such as manic depressive disorder and neurodegenerative diseases, and cardiomyocete hypertrophy [WO 99/65897; WO 00/38675; and Haq et al., *J. Cell Biol.* (2000) 151, 117]. These diseases may be caused by, or result in, the abnormal operation of certain cell signaling pathways in which GSK-3 plays a role. GSK-3 has been found to phosphorylate and modulate the activity of a number of regulatory proteins. These include glycogen synthase which is the rate limiting enzyme necessary for glycogen synthesis, the microtubule associated protein Tau, the gene transcription factor $\beta$-catenin, the translation initiation factor e1F2B, as well as ATP citrate lyase, axin, heat shock factor-1, c-Jun, c-Myc, c-Myb, CREB, and CEPB$\alpha$. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS*, 93, 8455–9 (1996); Cross et al., *Biochem. J.*, 303, 21–26 (1994); Cohen, *Biochem. Soc. Trans.*, 21, 555–567 (1993); Massillon et al., *Biochem J.* 299, 123–128 (1994)]. However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [WO 00/38675]. Therapeutic inhibitors of GSK-3 are therefore potentially useful for treating diabetic patients suffering from an impaired response to insulin.

GSK-3 activity has also been associated with Alzheimer's disease. This disease is characterized by the well-known $\beta$-amyloid peptide and the formation of intracellular neurofibrillary tangles. The neurofibrillary tangles contain hyperphosphorylated Tau protein where Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Current Biology* 4, 1077–86 (1994); Brownlees et al., *Neuroreport* 8, 3251–55 (1997)]. Therefore, it is believed that GSK-3 activity may promote generation of the neurofibrillary tangles and the progression of Alzheimer's disease.

Another substrate of GSK-3 is $\beta$-catenin which is degradated after phosphorylation by GSK-3. Reduced levels of $\beta$-catenin have been reported in schizophrenic patients and have also been associated with other diseases related to increase in neuronal cell death [Zhong et al., *Nature*, 395, 698–702 (1998); Takashima et al., *PNAS*, 90, 7789–93 (1993); Pei et al., *J. Neuropathol. Exp*, 56, 70–78 (1997)].

Aurora-2 is a serine/threonine protein kinase that has been implicated in human cancer, such as colon, breast and other solid tumors. This kinase is involved in protein phosphorylation events that regulate the cell cycle. Specifically, Aurora-2 plays a role in controlling the accurate segregation of chromosomes during mitosis. Misregulation of the cell cycle can lead to cellular proliferation and other abnormalities. In human colon cancer tissue, the aurora-2 protein has been found to be overexpressed [Bischoff et al., *EMBO J.*, 17, 3052–3065 (1998); Schumacher et al., *J. Cell Biol.*, 143, 1635–1646 (1998); Kimura et al., *J. Biol. Chem.*, 272, 13766–13771 (1997)].

Syk is a tyrosine kinase that plays a critical role in FcεRI mediated mast cell degranulation and eosiniphil activation. Accordingly, Syk kinase is implicated in various allergic disorders, in particular asthma.

It has been shown that Syk binds to the phosphorylated gamma chain of the FceR1 receptor via N-terminal SH2 domains and is essential for downstream signaling [Taylor et al, Mol Cell Biol 1995; 15:4149].

Inhibition of eosinophil apoptosis has been proposed as key mechanisms for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense)[Yousefi et al, J Exp Med 1996;183:1407].

The role of Syk in FcγR dependent and independent response in bone marrow derived macrophages has been determined by using irradiated mouse chimeras reconstituted with fetal liver cells from Syk –/– embryos. Syk deficient macrophages were defective in phagocytosis induced by FcγR but showed normal phagocytosis in response to complement [Kiefer et al, Mol Cell Biol 1998; 18:4209]. It has also been reported that aerosolized Syk antisense suppresses Syk expression and mediator release from macrophages [Stenton et al, J Immunology 2000; 164: 3790].

Considering the lack of currently available treatment options for the majority of the conditions associated with protein kinases, especially GSK-3, Aurora-2, and Syk, there is still a great need for new therapeutic agents that inhibit these protein targets.

SUMMARY OF THE INVENTION

The present invention addresses this need by providing a compound of formula I:

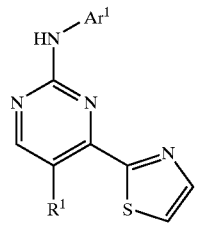

I or a pharmaceutically acceptable derivative thereof, wherein $R^1$ and $Ar^1$ are as defined below.

The present invention also provides a pharmaceutically acceptable composition comprising a compound of formula I.

The compounds and pharmaceutically acceptable compositions of the present invention are useful as inhibitors of GSK-3, Aurora-2, and Syk protein kinases. Thus, they are also useful in methods for treating or lessening the severity of a variety of disorders, such as allergic diseases, proliferative disorders, cancer, neurodegenerative disorders, and diabetes.

DESCRIPTION OF THE INVENTION

The present invention relates to a compound of formula I:

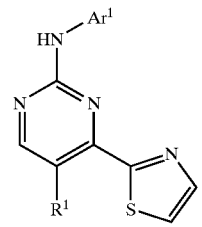

I or a pharmaceutically acceptable derivative thereof, wherein:

$R^1$ is selected from R, halogen, CN, $NO_2$, or TR;

T is an optionally substituted $C_1$–$C_4$ alkylidene chain wherein up to two methylene units of T are optionally and independently replaced by O, N(R), C(O), S, SO, or $SO_2$;

each R is independently selected from hydrogen or an optionally substituted $C_{1-6}$ aliphatic group, wherein:
  two R bound to the same nitrogen atom are optionally taken together with the nitrogen to form a 3–7 membered saturated, partially unsaturated, or fully unsaturated ring having 0–2 heteroatoms, in addition to the nitrogen bound thereto, independently selected from nitrogen, oxygen, or sulfur;

$Ar^1$ is an optionally substituted ring selected from:
  (a) a 3–8 membered monocyclic or 8–10 membered bicyclic saturated, partially unsaturated, or aryl ring;
  (b) a 3–7 membered heterocyclic ring having 1–3 heteroatoms independently selected from nitrogen, oxygen, or sulfur; or
  (c) a 5–6 membered monocyclic or 8–10 membered bicyclic heteroaryl ring having 1–4 heteroatoms independently selected from nitrogen, oxygen, or sulfur, wherein:
    $Ar^1$ is optionally substituted by one to four substituents selected from the group consisting of:
      (a) one group selected from QR, $Ar^2$, or $QAr^2$; and
      (b) up to four $R^2$ groups;

each Q is indpendently selected from a valence bond or an optionally substituted $C_{1-6}$ alkylidene chain, wherein:
  one or two non-adjacent methylene units of Q are optionally and independently replaced by —O—, —S—, —NR—, —C(O)—, —CO$_2$—, —C(O)NR—, —OC(O)NR—, —C(O)C(O)—, —C(O)C(O)—, —NRC(O)—, NRCO$_2$—, —NRC(O)NR—, —S(O)—, —SO$_2$—, —NRSO$_2$—, —SO$_2$NR—, or —NRSO$_2$NR—;

each $Ar^2$ is an optionally substituted ring independently selected from:
  (a) a 3–8 membered monocyclic or 8–10 membered bicyclic saturated, partially unsaturated, or aryl ring;
  (b) a 3–7 membered heterocyclic ring having 1–3 heteroatoms independently selected from nitrogen, oxygen, or sulfur; or
  (c) a 5–6 membered monocyclic or 8–10 membered bicyclic heteroaryl ring having 1–4 heteroatoms independently selected from nitrogen, oxygen, or sulfur, wherein:
    $Ar^2$ is optionally substituted by one to four $R^2$ groups; and each $R^2$ is independently selected from R, halogen, $NO_2$, CN, OR, SR, $N(R)_2$, NRCOR, $NRCON(R)_2$, $NRCO_2R$, C(O)R, $CO_2R$, $CON(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$; wherein:

two $R^2$ on adjacent positions on $Ar^1$ or $Ar^2$ are optionally taken together to form a saturated, partially unsaturated, or fully unsaturated 4–6 membered ring having 0–3 heteroatoms independently selected from nitrogen, oxygen, or sulfur.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group" as used herein means a straight-chain or branched $C_1$–$C_8$ hydrocarbon chain that is completely saturated or that contains one or more units of unsaturation, or a monocyclic $C_3$–$C_8$ hydrocarbon or bicyclic $C_8$–$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3–7 members. For example, suitable aliphatic groups include, but are not limited to, linear or branched or alkyl, alkenyl, alkynyl groups and hybrids thereof such as (cycloalkyl)alkyl, (cycloalkenyl) alkyl or (cycloalkyl)alkenyl.

The terms "alkyl", "alkoxy", "hydroxyalkyl", "alkoxyalkyl", and "alkoxycarbonyl", used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are selected from halogen, —R°, —OR°, —SR°, 1,2-methylene-dioxy, 1,2-ethylenedioxy, phenyl (Ph) optionally substituted with R°, —O(Ph) optionally substituted with R°, —$CH_2$(Ph) optionally substituted with R°, —$CH_2CH_2$(Ph), optionally substituted with R°, —$NO_2$, —CN, —$N(R°)_2$, —NR°C(O)R°, —NR°C(O)N(R°)$_2$, —NR°$CO_2$R°, —NR°NR°C(O)R°, —NR°NR°C(O)N(R°)$_2$, —NR°NR°$CO_2$R°, —C(O)C(O)R°, —C(O)$CH_2$C(O)R°, —$CO_2$R°, —C(O)R°, —C(O)N(R°)$_2$, —OC(O)N(R°)$_2$, —S(O)$_2$R°, —$SO_2$N(R°)$_2$, —S(O)R°, —NR°$SO_2$N(R°)$_2$, —NR°$SO_2$R°, —C(=S)N(R°)$_2$, —C(=NH)—N(R°)$_2$, or —$(CH_2)_y$NHC(O)R°, wherein each R° is independently selected from hydrogen, optionally substituted $C_{1-6}$ aliphatic, an unsubstituted 5–6 membered heteroaryl or heterocyclic ring, phenyl, —O(Ph), or —$CH_2$(Ph). Optional substituents on the aliphatic group of R° are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo $C_{1-4}$ aliphatic.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo ($C_{1-4}$ aliphatic).

Optional substituents on the nitrogen of a non-aromatic heterocyclic ring are selected from —R+, —N(R+)$_2$, —C(O)R+, —$CO_2$R+, —C(O)C(O)R+, —C(O)$CH_2$C(O)R+, —$SO_2$R+, —$SO_2$N(R+)$_2$, —C(=S)N(R+)$_2$, —C(=NH)—N(R+)$_2$, or —NR+$SO_2$R+; wherein R+ is hydrogen, an optionally substituted $C_{1-6}$ aliphatic, optionally substituted phenyl, optionally substituted —O(Ph), optionally substituted —$CH_2$(Ph), optionally substituted —$CH_2CH_2$(Ph), or an unsubstituted 5–6 membered heteroaryl or heterocyclic ring. Optional substituents on the aliphatic group or the phenyl ring of R+are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo($C_{1-4}$ aliphatic).

The term "alkylidene chain" refers to a straight or branched carbon chain that may be fully saturated or have one or more units of unsaturation and has two points of attachment to the rest of the molecule.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention. Such compounds are useful, for example, as analytical tools or probes in biological assays.

According to one embodiment, the present invention relates to a compound of formula I:

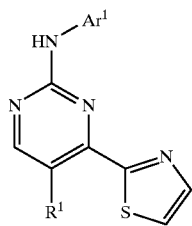

I or a pharmaceutically acceptable derivative thereof, wherein $R^1$ and $Ar^1$ are as defined above, provided that: when $Ar^1$ is phenyl with two $R^2$ substituents, then the two $R^2$ are not simultaneously OR in the meta and para positions of $Ar^1$.

According to another embodiment, the present invention relates to a compound of formula I:

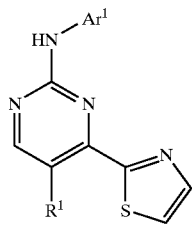

I or a pharmaceutically acceptable derivative thereof, wherein $R^1$ and $Ar^1$ are as defined above, provided that: $R^1$ is other than CN.

Preferred $Ar^1$ groups of formula I are optionally substituted rings selected from:

(a) a phenyl, indanyl, or naphthyl ring;
(b) a 5–6 membered heterocyclic ring having 1–3 heteroatoms independently selected from nitrogen, oxygen, or sulfur; or
(c) a 5–6 membered monocyclic or 9–10 membered bicyclic heteroaryl ring having 1–2 heteroatoms independently selected from oxygen, nitrogen, or sulfur.

More preferred $Ar^1$ groups of formula I are rings selected from:

(a) a phenyl, indanyl, or naphthyl ring;
(b) a 5–6 membered heterocyclic ring having 1–3 heteroatoms independently selected from nitrogen, oxygen, or sulfur; or
(c) a 5–6 membered monocyclic heteroaryl ring having 1–2 nitrogens, wherein:

$Ar^1$ is substituted by one to four substituents selected from the group consisting of:
(a) one group selected from QR, $Ar^2$, or $QAr^2$; and
(b) up to four $R^2$ groups.

Most preferred $Ar^1$ rings are selected from substituted phenyl, indanyl, naphthyl, pyrimidinyl, or pyridyl. Preferred $R^2$ substituents on $Ar^1$ are halogen, CN, $CO_2R$, R, $NO_2$, OR, haloalkyl, $SO_2N(R)_2$, or $N(R)_2$. More preferred $R^2$ substituents on $Ar^1$ are fluoro, iodo, chloro, bromo, $CO_2CH_3$, methyl, ethyl, t-butyl, $NH_2$, NHMe, $N(Me)_2$, OH, $OCH_3$, $OCH_2CH_3$, $CF_3$, $SO_2NH_2$, or $SO_2NHMe$. Other preferred compounds include those where two R are taken together to form a methylenedioxy or an ethylenedioxy substituent.

Preferred QR or $QAr^2$ substituents on $Ar^1$ of formula I are those wherein Q is a $C_{1-4}$ alkylidene chain wherein one or two methylene units of Q are optionally replaced by O, NR, NRCO, $NRCO_2$, $NRSO_2$, or CONR, wherein each R is hydrogen or an optionally substituted $C_{1-4}$ aliphatic group and wherein $Ar^2$ is a 3–6 membered carbocyclic ring or an optionally substituted phenyl, 5–6 membered heterocyclic, or heteroaryl ring having one to two heteroatoms independently selected from nitrogen, oxygen, or sulfur.

The $Ar^2$ group of the $QAr^2$ moiety of formula I is optionally substituted with R, OR, $N(R)_2$, $SO_2R$, halogen, $NO_2$, CN, SR, $SO_2N(R)_2$, $CO_2R$, C(O)R, or oxo. More preferred $QAr^2$ groups of formula I are selected from $O(CH_2)_3$pyrrolidin-1-yl, $O(CH_2)_2$morpholin-4-yl, $O(CH_2)_3$(4-hydroxyethylpiperazin-1-yl), $O(CH_2)_3$piperazin-1-yl, $O(CH_2)_3$(4-hydroxymethylpiperidin-1-yl), $O(CH_2)_3$(4-hydroxypiperidin-1-yl), $NHCOCH_2$pyridin-2-yl, $NHCOCH_2$(2-aminothiazol-4-yl), $NHCOCH_2$cyclopropyl, $NHCO(CH_2)_2$(piperazin-2,5-dione-3-yl), NHCOpyrrolidin-1-yl, NHCOmorpholin-4-yl, $NHCO_2CH_2$tetrahydrofuran-2-yl, $NHCO_2$tetrahydrofuran-2-yl, $NHCO_2$tetrahydropyran-4-yl, $NHCO_2CH_2$tetrahydropyran-2-yl, Ophenyl, $OCH_2$ (cyclohexyl), $OCH_2$phenyl, $OCH_2$ (3-CN-phenyl), $OCH_2$ (2-$NO_2$-phenyl), $OCH_2$ (3-$NH_2$-phenyl), $OCH_2$(4-$CO_2R$-phenyl), $OCH_2$-pyridyl, $OCH_2$(mono-, di-, or tri-halogenated phenyl), $OCH_2(C_1-C_6$ aliphatic substituted phenyl), $OCH_2CH_2$-pyrrolyl, $OCH_2$-pyrrolyl, and $OCH_2$ (phenyl substituted with one or two $R^2$)

Preferred $Ar^2$ substituents on $Ar^1$ of formula I are optionally substituted rings selected from:

(a) a phenyl, indanyl, or naphthyl ring;
(b) a 5–6 membered heterocyclic ring having 1–3 heteroatoms independently selected from nitrogen, oxygen, or sulfur; or
(c) a 5–6 membered monocyclic or 9–10 membered bicyclic heteroaryl ring having 1–2 heteroatoms independently selected from oxygen, nitrogen, or sulfur, wherein:

$Ar^2$ is optionally substituted with 1–2 $R^2$ groups.

More preferred $Ar^2$ substituents on $Ar^1$ of formula I are optionally substituted rings selected from phenyl, pyridyl, indolyl, naphthyl, or benzo[1,3]dioxolyl.

Preferred $R^2$ groups, when present, on the $Ar^2$ substituent on $Ar^1$ of formula I are selected from R, halogen, $NO_2$, CN, OR, SR, $N(R)_2$, C(O)R, $SO_2N(R)_2$, or $SO_2R$. More preferred $R^2$ groups, when present, on the $Ar^2$ substituent on $Ar^1$ of formula I are selected from methyl, ethyl, t-butyl, fluoro, chloro, bromo, $CF_3$, OMe, OEt, CN, $SO_2Me$, $SO_2NH_2$, $NH_2$, NHMe, $N(Me)_2$, SMe, SEt, OH, C(O)Me, $NO_2$, or $CH_2OH$.

One embodiment of this invention relates to a compound of formula Ia:

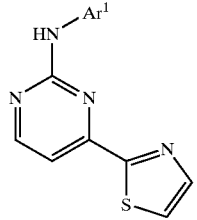

Ia or a pharmaceutically acceptable derivative thereof, wherein Ar¹ is as defined above.

Preferred Ar¹ groups of formula Ia are those described above for formula I.

Another embodiment of this invention relates to a compound of formula II:

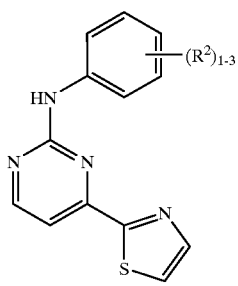

II or a pharmaceutically acceptable derivative thereof, wherein R² is as defined above.

Preferred R² groups of formula II are those defined above for formula I and include those where two R² are taken together to form a methylenedioxy or an ethylenedioxy substituent.

A preferred embodiment of this invention relates to a compound of formula IIa or IIa':

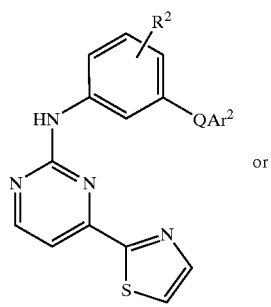

IIa or

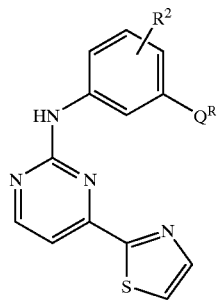

IIa' or a pharmaceutically acceptable derivative thereof, wherein QR, QAr² and R² are as defined above.

Preferred R² groups of formula IIa or IIa' are those described above for compounds of formula I.

Preferred QR and QAr² groups of formula IIa or IIa' are those described above for compounds of formula I.

Another preferred embodiment relates to a compound of formula III:

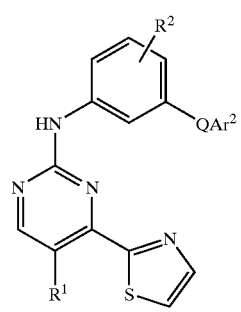

III or a pharmaceutically acceptable derivative thereof, wherein R¹, R², and QAr² are as defined above.

Preferred R² and QAr² groups of formula III are those described above for formula I.

Preferred R¹ groups of formula III are selected from hydrogen, N(R)₂, SR, OR, or TR. More preferred R¹ groups are selected from OH, OCH₃, CH₂OH, CH₂OCH₃, CH₂NH₂, or CH₂NHCH₃.

Another preferred embodiment relates to a compound of formula IV:

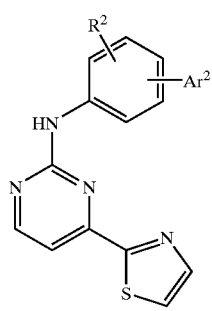

IV or a pharmaceutically acceptable derivative thereof, wherein R² and Ar² are as defined above.

Preferred R² and Ar² groups of formula IV are those described above for compounds of formula I.

Exemplary structures of formula I are set forth in Table 1 below.
TABLE 1
Compounds of Formula I
| Cmpd I- | Structure |
|---|---|
| 1 | 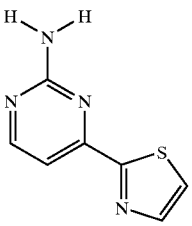 |
| 2 | 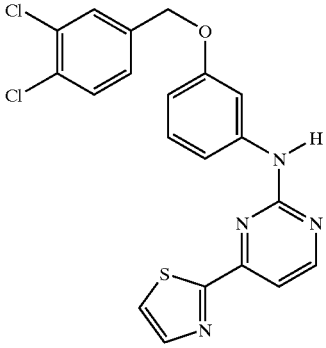 |
| 3 | 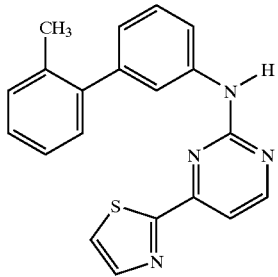 |
| 4 | 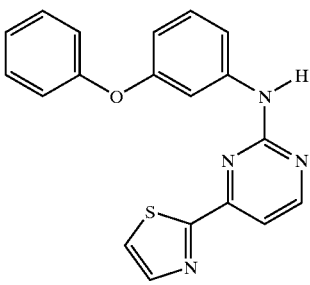 |
TABLE 1-continued
Compounds of Formula I
| Cmpd I- | Structure |
|---|---|
| 5 | 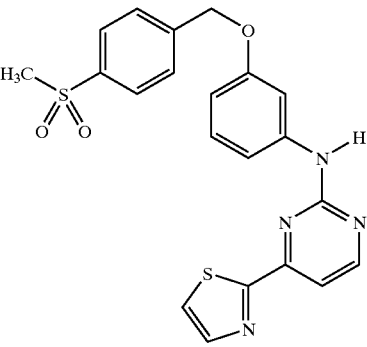 |
| 6 | 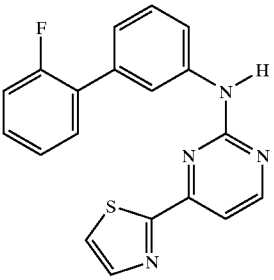 |
| 7 | 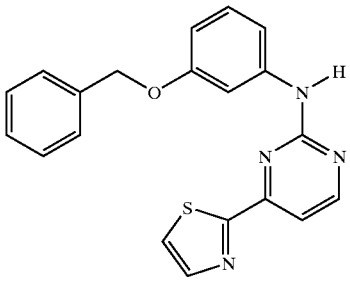 |
| 8 | 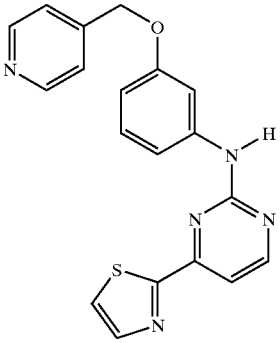 |

TABLE 1-continued
Compounds of Formula I
| Cmpd I- | Structure |
|---|---|
| 9 | 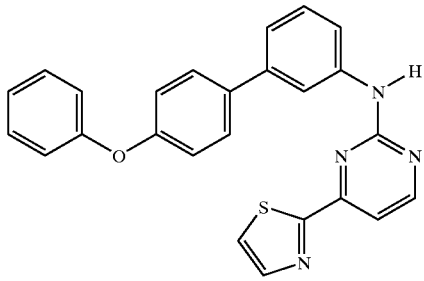 |
| 10 | 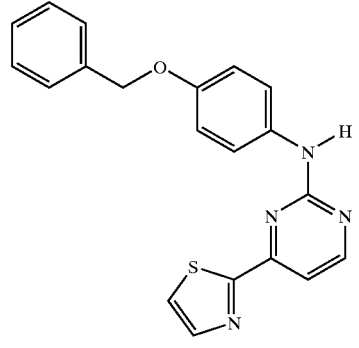 |
| 11 | 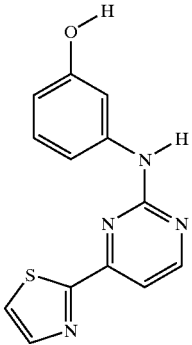 |
| 12 | 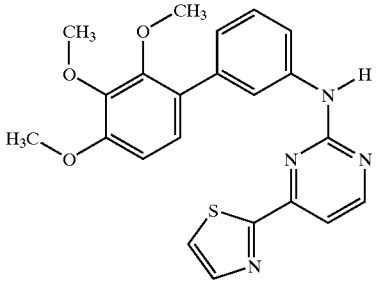 |
| 13 | 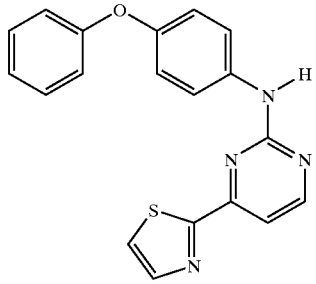 |
| 14 | 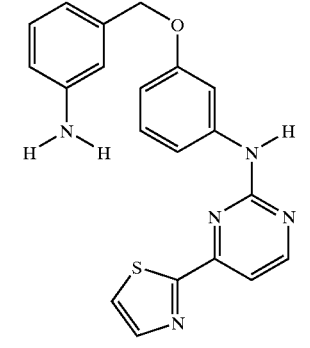 |
| 15 | 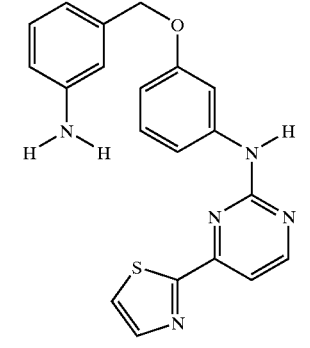 |
| 16 | 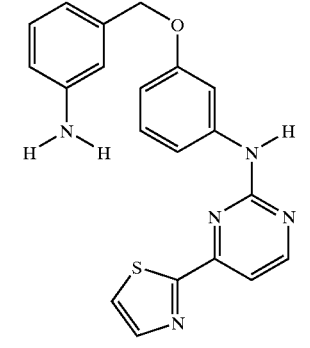 |

TABLE 1-continued

Compounds of Formula I

| Cmpd I- | Structure |
|---|---|
| 17 | 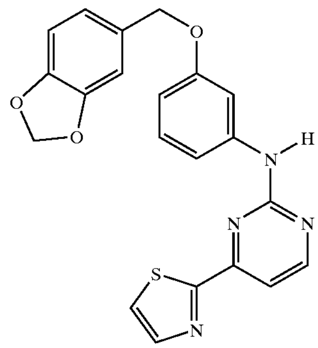 |
| 18 | 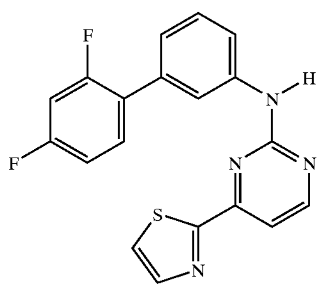 |
| 19 | 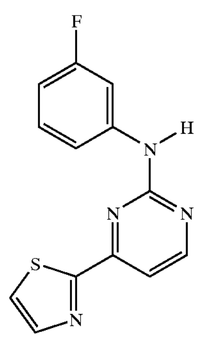 |
| 20 | 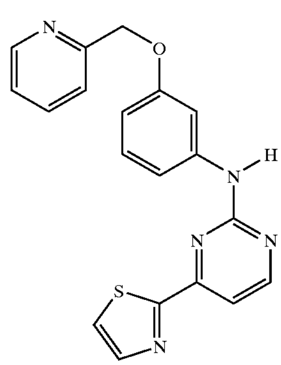 |
| 21 | |
| 22 | |
| 23 | |
| 24 | |

TABLE 1-continued
Compounds of Formula I
| Cmpd I- | Structure |
|---|---|
| 25 | 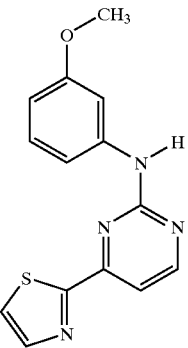 |
| 26 | 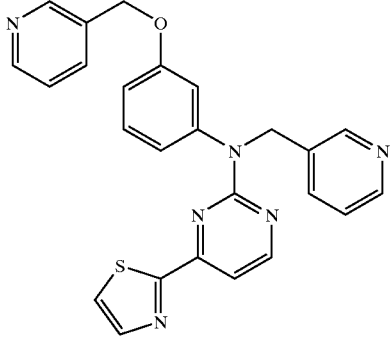 |
| 27 | 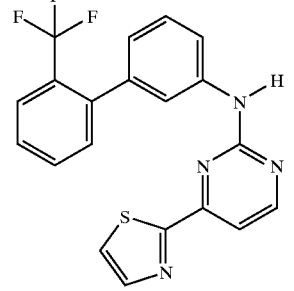 |
| 28 | 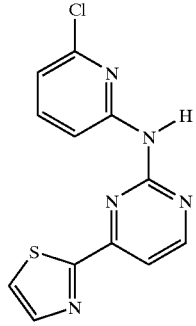 |
| 29 | 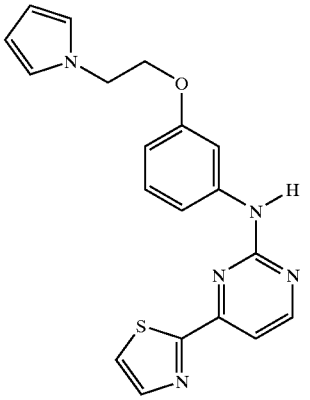 |
| 30 | 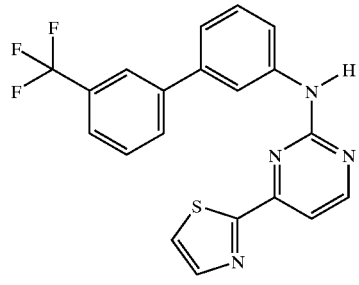 |
| 31 | 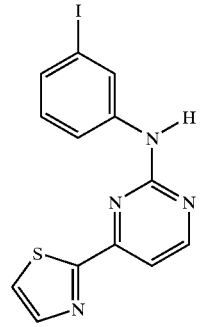 |
| 33 | 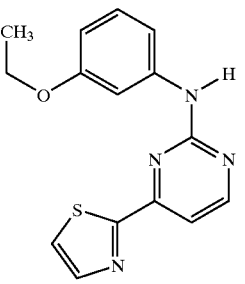 |

TABLE 1-continued

Compounds of Formula I

| Cmpd I- | Structure |
|---|---|
| 34 | 3-bromophenyl-NH-pyrimidine-thiazole |
| 35 | 2-nitrobenzyloxy-3-phenyl-NH-pyrimidine-thiazole |
| 36 | 2-ethoxybiphenyl-NH-pyrimidine-thiazole |
| 37 | 3-(trifluoromethyl)phenyl-NH-pyrimidine-thiazole |
| 38 | 2-aminobenzyloxy-3-phenyl-NH-pyrimidine-thiazole |
| 39 | 2,5-dimethylbiphenyl-NH-pyrimidine-thiazole |
| 40 | 4-nitrophenyl-NH-pyrimidine-thiazole |
| 41 | 2-fluorobenzyloxy-3-phenyl-NH-pyrimidine-thiazole |

TABLE 1-continued

Compounds of Formula I

| Cmpd I- | Structure |
|---|---|
| 42 | (3-ethoxybiphenyl-3-yl)-[4-(thiazol-2-yl)pyrimidin-2-yl]amine |
| 43 | (4-fluorophenyl)-[4-(thiazol-2-yl)pyrimidin-2-yl]amine |
| 44 | {3-[(2-methoxybenzyl)oxy]phenyl}-[4-(thiazol-2-yl)pyrimidin-2-yl]amine |
| 45 | [3'-(methylsulfonyl)biphenyl-3-yl]-[4-(thiazol-2-yl)pyrimidin-2-yl]amine |
| 46 | (4-chlorophenyl)-[4-(thiazol-2-yl)pyrimidin-2-yl]amine |
| 47 | {3-[(2-trifluoromethylbenzyl)oxy]phenyl}-[4-(thiazol-2-yl)pyrimidin-2-yl]amine |
| 48 | (4'-cyanobiphenyl-3-yl)-[4-(thiazol-2-yl)pyrimidin-2-yl]amine |
| 49 | (3,4-difluorophenyl)-[4-(thiazol-2-yl)pyrimidin-2-yl]amine |

TABLE 1-continued

Compounds of Formula I

| Cmpd I- | Structure |
|---|---|
| 50 | (structure) |
| 51 | (structure) |
| 52 | (structure) |
| 53 | (structure) |
| 54 | (structure) |
| 55 | (structure) |
| 56 | (structure) |
| 57 | (structure) |
| 58 | (structure) |

TABLE 1-continued

Compounds of Formula I

| Cmpd I- | Structure |
|---|---|
| 59 | (structure) |
| 60 | (structure) |
| 61 | (structure) |
| 62 | (structure) |
| 63 | (structure) |
| 64 | (structure) |
| 65 | (structure) |
| 66 | (structure) |
| 67 | (structure) |

TABLE 1-continued

Compounds of Formula I

| Cmpd I- | Structure |
|---|---|
| 68 | (structure) |
| 69 | (structure) |
| 70 | (structure) |
| 71 | (structure) |
| 72 | (structure) |
| 73 | (structure) |
| 74 | (structure) |
| 75 | (structure) |

TABLE 1-continued
Compounds of Formula I
| Cmpd I- | Structure |
|---|---|
| 76 | 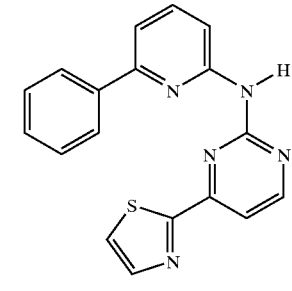 |
| 77 | 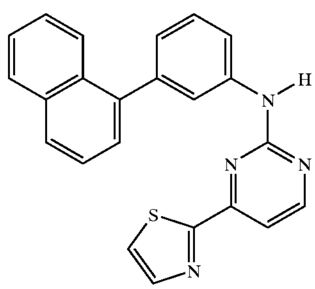 |
| 78 | 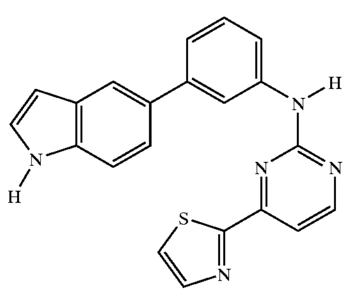 |
| 79 | 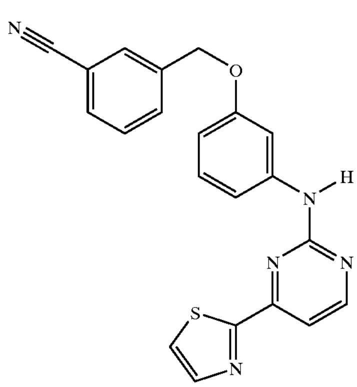 |
| 80 | 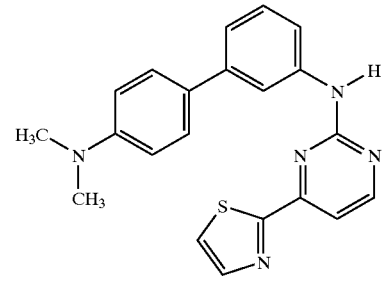 |
| 81 | 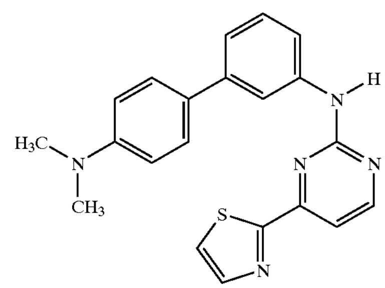 |
| 82 | 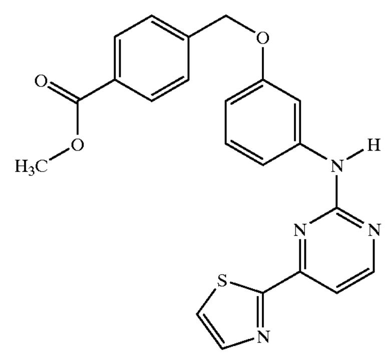 |
| 83 | 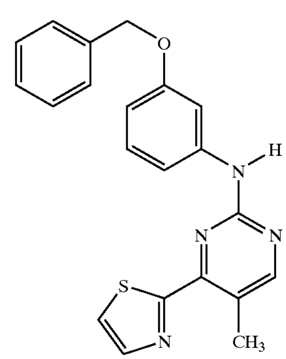 |

TABLE 1-continued

Compounds of Formula I

| Cmpd I- | Structure |
|---|---|
| 84 | 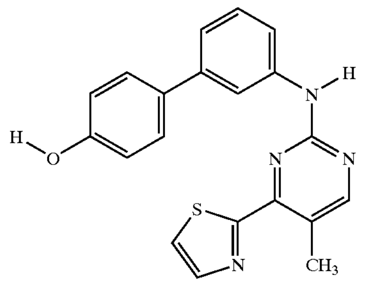 |
| 85 | 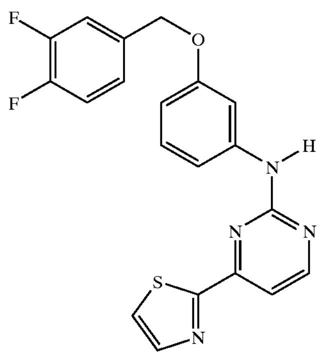 |
| 86 | 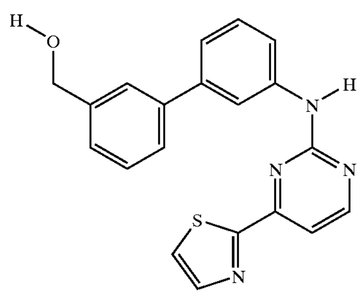 |
| 87 | 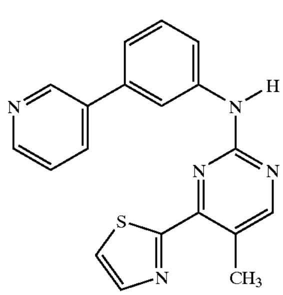 |
| 88 | 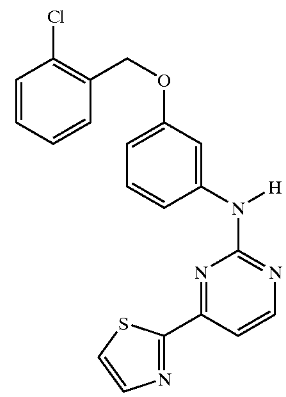 |
| 89 | 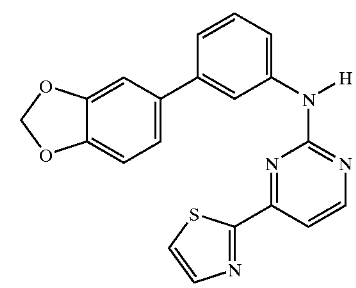 |
| 90 | 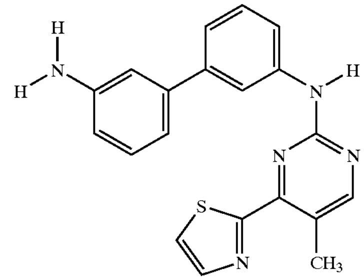 |
| 91 | 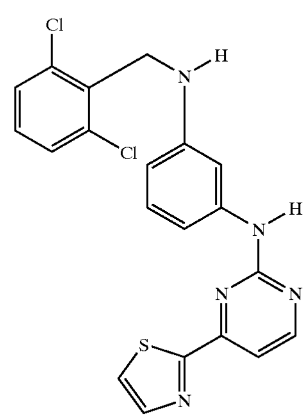 |

TABLE 1-continued
Compounds of Formula I
| Cmpd I- | Structure |
|---|---|
| 92 | 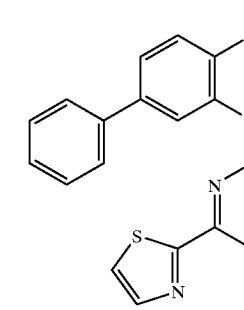 |
| 93 | 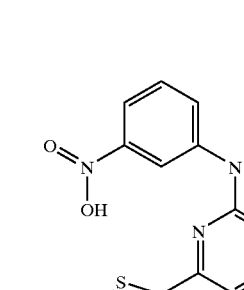 |
| 94 | 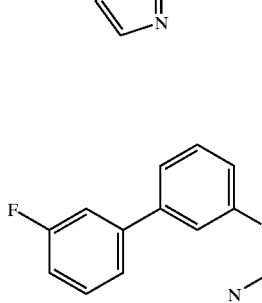 |
| 95 | 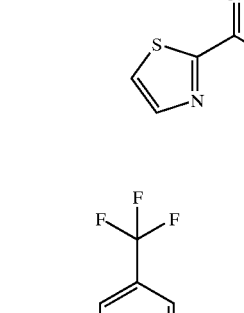 |
| 96 | |
| 97 | |
| 98 | |
| 99 | |

TABLE 1-continued
Compounds of Formula I
| Cmpd I- | Structure |
|---|---|
| 100 | 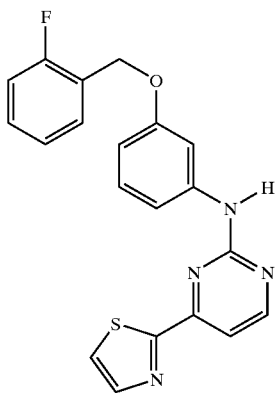 |
| 101 | 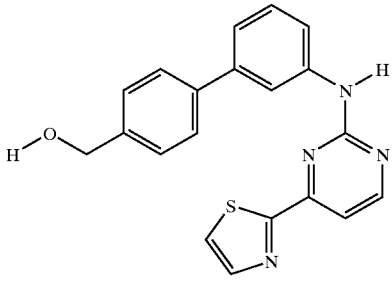 |
| 103 | 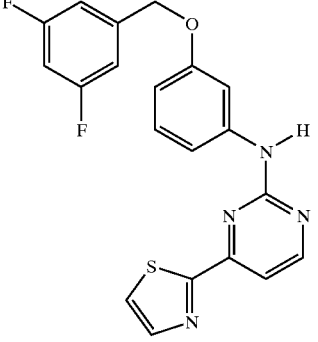 |
| 104 | 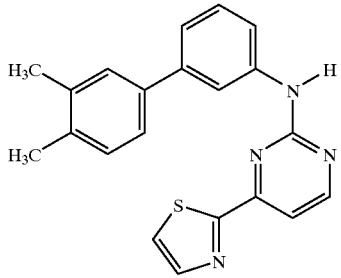 |
| 105 | 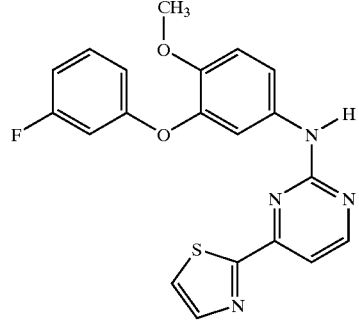 |
| 106 | 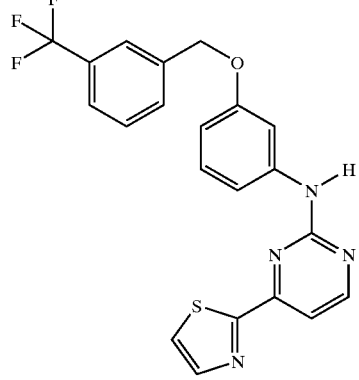 |
| 107 | 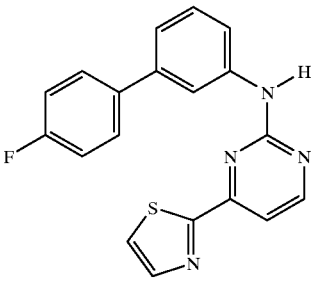 |
| 108 | 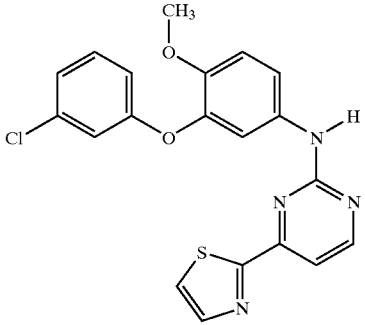 |

TABLE 1-continued

Compounds of Formula I

| Cmpd I- | Structure |
|---|---|
| 109 | *4-fluorobenzyloxy-phenyl linked to 2-amino-4-(thiazol-2-yl)pyrimidine* |
| 110 | *4-chlorobiphenyl-3-yl linked to 2-amino-4-(thiazol-2-yl)pyrimidine* |
| 111 | *3-(4-chlorophenoxy)-4-methoxyphenyl linked to 2-amino-4-(thiazol-2-yl)pyrimidine* |
| 112 | *2,3-dichlorobenzyloxy-phenyl linked to 2-amino-4-(thiazol-2-yl)pyrimidine* |
| 113 | *4'-methoxybiphenyl-3-yl linked to 2-amino-4-(thiazol-2-yl)pyrimidine* |
| 114 | *5-phenoxy-2-methoxyphenyl linked to 2-amino-4-(thiazol-2-yl)pyrimidine* |
| 115 | *2-methylbenzyloxy-phenyl linked to 2-amino-4-(thiazol-2-yl)pyrimidine* |
| 116 | *4'-methylbiphenyl-3-yl linked to 2-amino-4-(thiazol-2-yl)pyrimidine* |

TABLE 1-continued
Compounds of Formula I
| Cmpd I- | Structure |
|---|---|
| 117 | 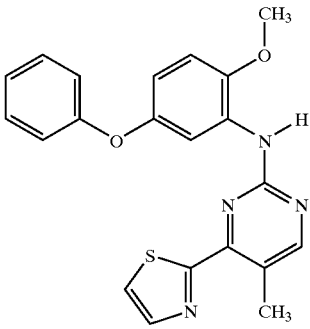 |
Exemplary structures of formulae IIa and IIa' are set forth in Table 2 below.
TABLE 2
Compounds of Formulae IIa and IIa'
| | |
|---|---|
| IIa-1 | 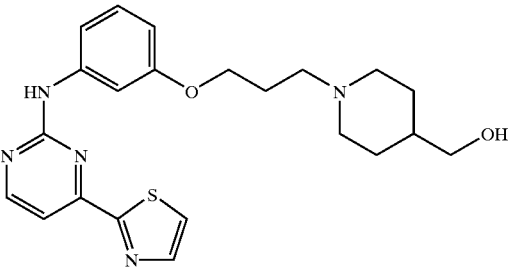 |
| IIa-2 | 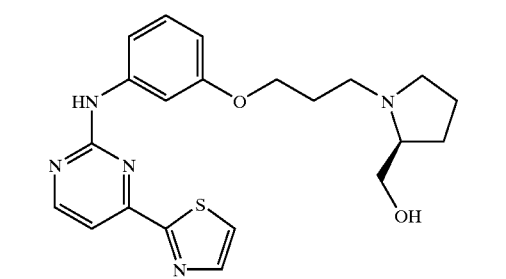 |
| IIa-3 | 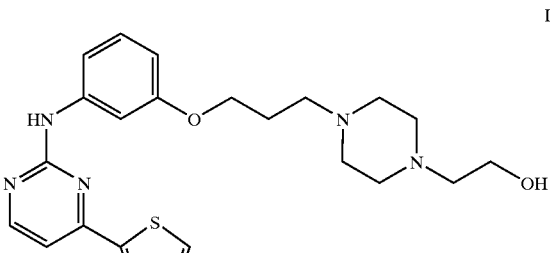 |
TABLE 2-continued
Compounds of Formulae IIa and IIa'
| | |
|---|---|
| IIa-4 | 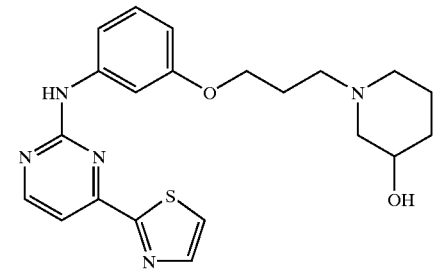 |
| IIa-5 | 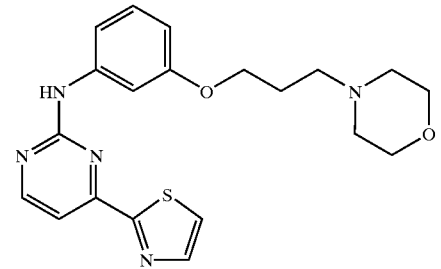 |
| IIa-6 | 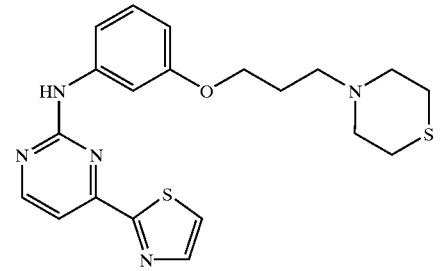 |
| IIa-7 | 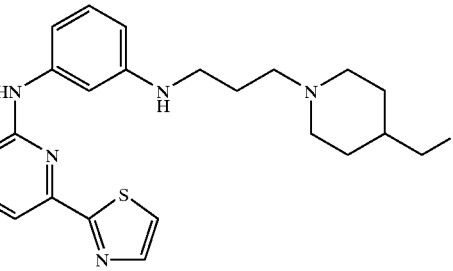 |
| IIa-8 | 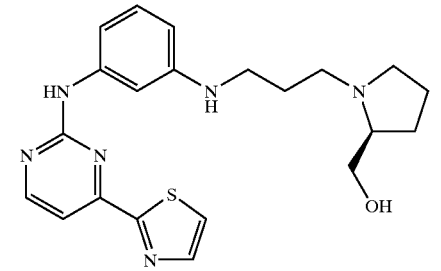 |

TABLE 2-continued
Compounds of Formulae IIa and IIa'
IIa-9
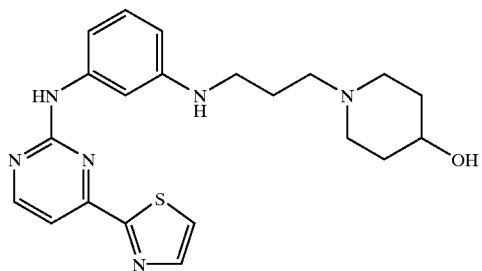
IIa-10
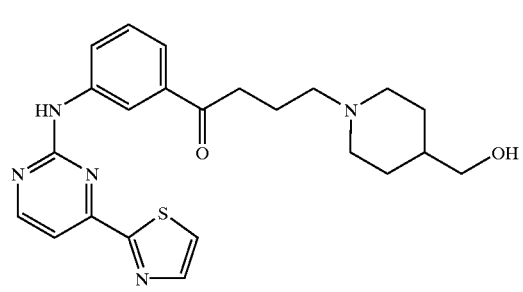
IIa-11
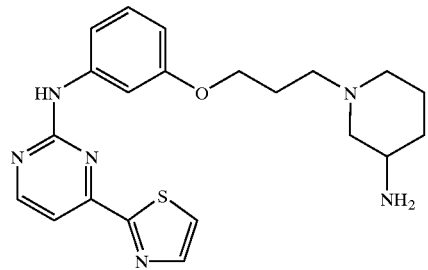
IIa-12
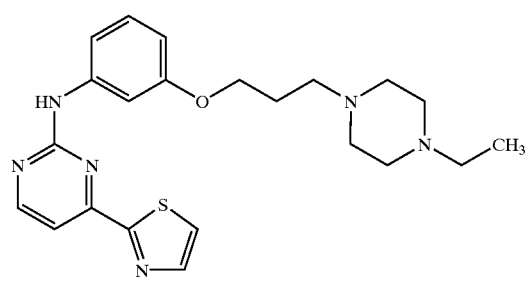
IIa-13
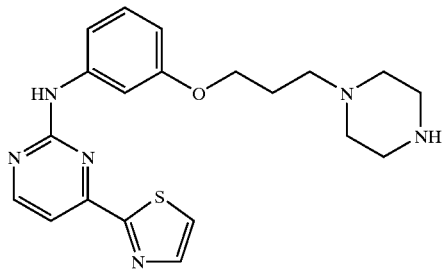
TABLE 2-continued
Compounds of Formulae IIa and IIa'
IIa-14
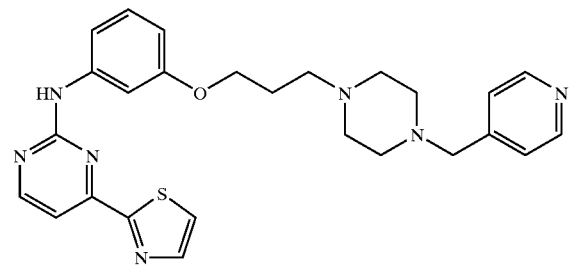
IIa-15
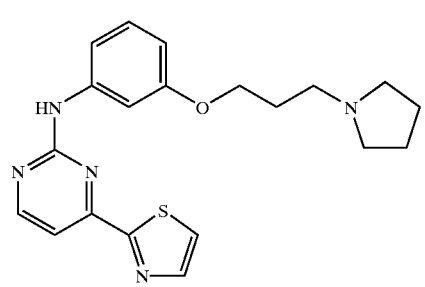
IIa-16
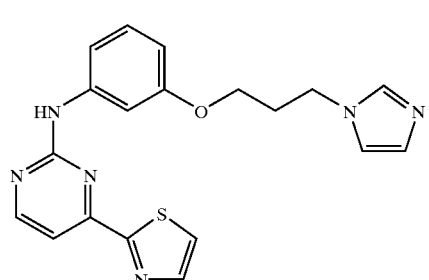
IIa-17
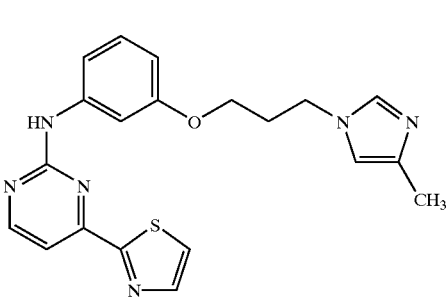
IIa-18
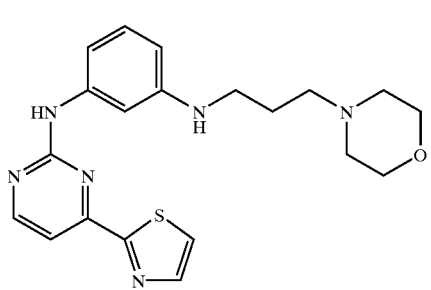

TABLE 2-continued
Compounds of Formulae IIa and IIa'
IIa-19
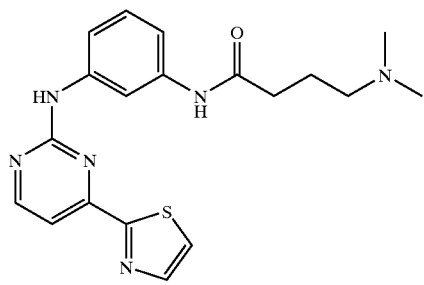
IIa-20
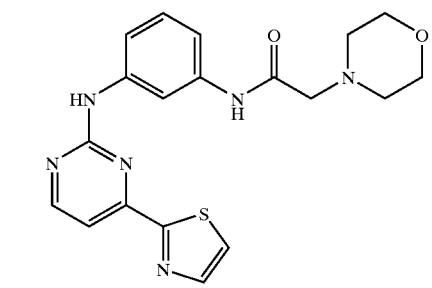
IIa-21
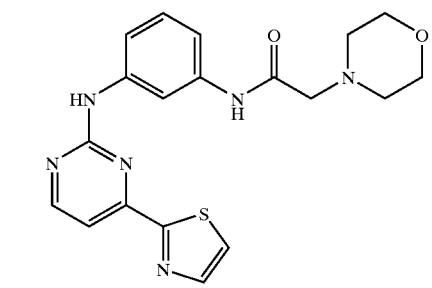
IIa-22
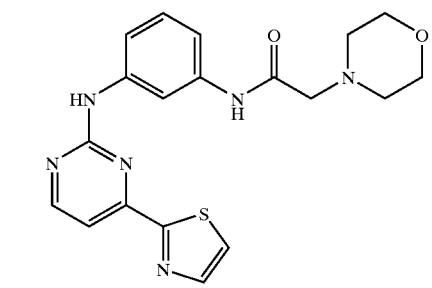
IIa-23
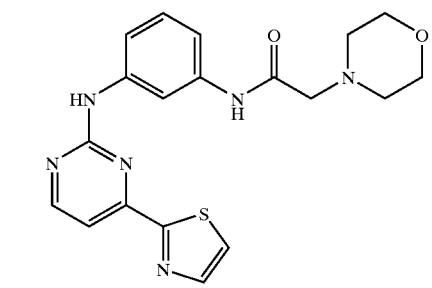
IIa-24
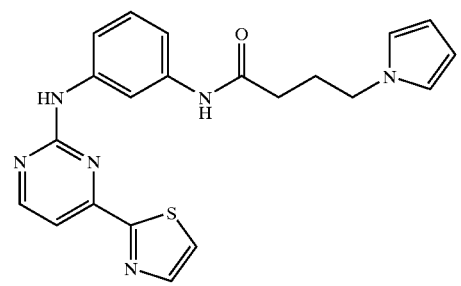
IIa-25
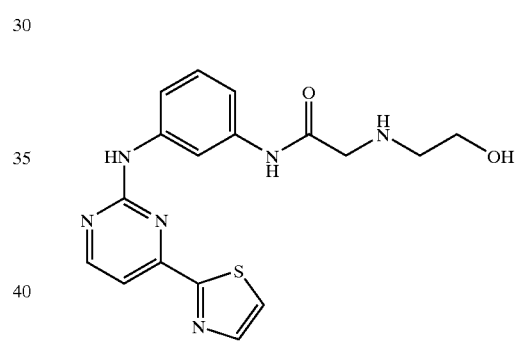
IIa-26
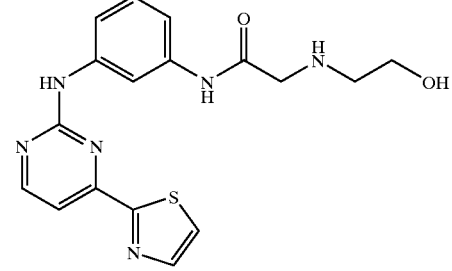
IIa-27
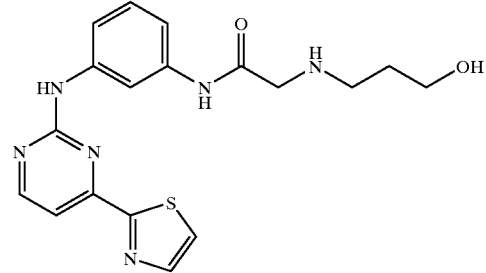
IIa-28
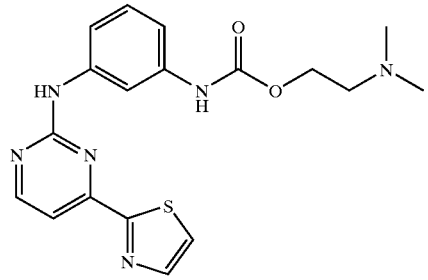

TABLE 2-continued

Compounds of Formulae IIa and IIa'

TABLE 2-continued

Compounds of Formulae IIa and IIa'

IIa-39, IIa-40, IIa-41, IIa-42, IIa-43, IIa-44, IIa-45, IIa-46, IIa-47

TABLE 2-continued

Compounds of Formulae IIa and IIa'

IIa-48

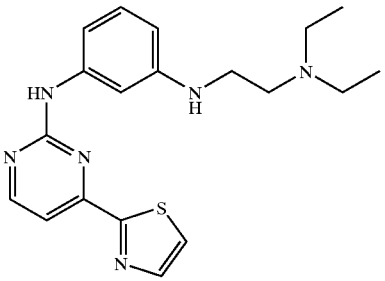

IIa-49

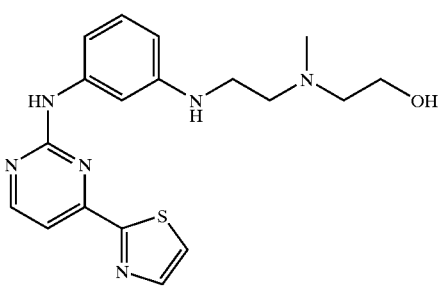

IIa-50

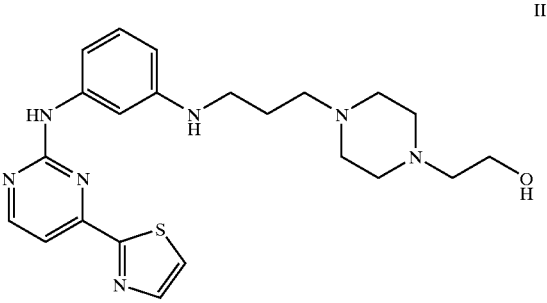

The present compounds may be prepared in general by methods known to those skilled in the art for analogous compounds, as illustrated by the general Scheme I and the synthetic examples shown below.

Reagents and conditions: (a) DMF-DMA, THF, 12–18 hours, room temperature; (b) H$_2$NCN, 4N HCl in dioxane, 12–18 hours, 120° C.; (c) Ethanol, reflux, 12–18 hours.

Scheme I above shows a general synthetic route that may be used used for preparing compounds of formula I.

In step (a), a solution of 2-acetyl thiazole (1) in THF is treated with dimethylformamide-dimethylacetal and the resulting mixture stirred at room temperature over night. The reaction mixture is concentrated in vacuo and the concentrate triturated with diethyl ether to afford 2.

To prepare intermediate 4 from aniline 3 in step (b), a mixture of 3 and cyanamide in HCl (4N in dioxane) is heated at 120° C. overnight. After cooling to room temperature, aqueous work-up affords the desired guanidine compound 4. One of skill in the art would recognize that a wide variety of aryl guanidines may be prepared at step (b) and, thus, be used to prepare compounds of formula I with a wide variety of Ar$^1$ rings.

In step (c), guanidine 4 is combined with enaminone 2 in ethanol in a sealed tube. The resulting mixture is heated at reflux overnight then concentrated and the crude product purified by column chromatography to afford the desired pyrimidine compound 5. The details of the conditions used for producing these compounds are set forth in the Examples.

The activity of a compound utilized in this invention as an inhibitor of GSK3, Aurora2, or Syk protein kinase may be assayed in vitro, in vivo or in a cell line according to methods known in the art and by the methods set forth in the Examples below. In vitro assays include assays that determine inhibition of either the phosphorylation activity or ATPase activity of activated GSK3, Aurora2, or Syk protein kinase. Alternate in vitro assays quantitate the ability of the inhibitor to bind to GSK3, Aurora2, or Syk protein kinase. Inhibitor binding may be measured by radiolabelling the inhibitor prior to binding, isolating the inhibitor/GSK3, inhibitor/Aurora2, or inhibitor/Syk complex and determining the amount of radiolabel bound. Alternatively, inhibitor binding may be determined by running a competition experiment where new inhibitors are incubated with GSK3, Aurora2, or Syk protein kinase bound to known radioligands. Detailed conditions for assaying a compound utilized in this invention as an inhibitor of GSK3, Aurora2, or Syk protein kinase are set forth in the Examples below.

According to another embodiment, the present invention provides a composition, or pharmaceutically acceptable composition, comprising a compound of this invention or a pharmaceutically acceptable derivative thereof and a phar- Scheme I

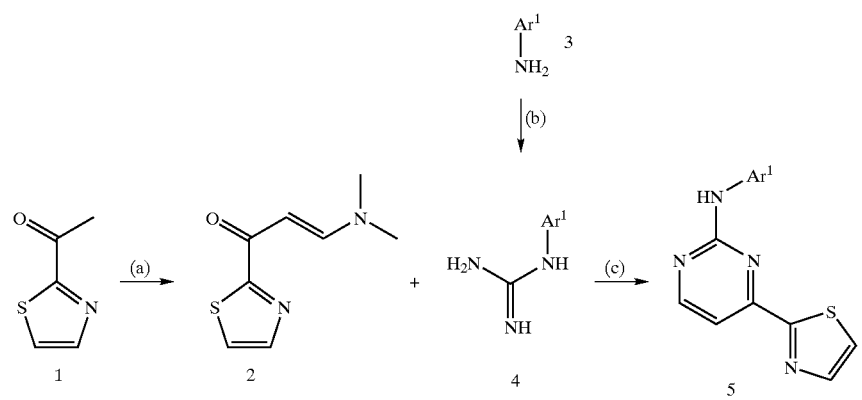

maceutically acceptable carrier, adjuvant, or vehicle. The amount of compound in the compositions of this invention is such that is effective to detectably inhibit a protein kinase, particularly GSK3, Aurora2, or Syk protein kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in GSK3, Aurora2, or Syk protein kinase activity between a sample comprising said composition and a GSK3, Aurora2, or Syk protein kinase and an equivalent sample comprising GSK3, Aurora2, or Syk protein kinase in the absence of said composition.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a GSK3, Aurora2, or Syk protein kinase.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+$ $(C_{1-4}$ alkyl$)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, in the treatment of diabetes other antidiabetic agents may be combined with the compounds of this invention to treat diabetes. These agents include, without limitation, insulin in injectable or inhalation form, insulin analogues, glitazones, sulfonyl ureas, alpha glucosidase inhibitors, biguanides, and insulin sensitizers.

Other examples of agents the inhibitors of this invention may also be combined with include, without limitation: chemotherapeutic agents such as Gleevec™, adriamycin, dexamethasone, vincristine, cyclophosphamide, fluorouracil, topotecan, taxol, interferons, and platinum derivatives; treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting GSK3 protein kinase activity in a biological sample comprising the step of contacting said biological sample with a compound of this invention, or a composition comprising said compound.

According to another embodiment, the invention relates to a method of inhibiting Aurora2 protein kinase activity in a biological sample comprising the step of contacting said biological sample with a compound of this invention, or a composition comprising said compound.

According to another embodiment, the invention relates to a method of inhibiting Syk protein kinase activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of GSK3, Aurora2, or Syk protein kinase activity in a biological sample is useful for a variety of purposes that are known to one of skill in the art. Examples of such purposes include, but are not limited to, blood transfusion, organ-transplantation, biological specimen storage, and biological assays.

According to another embodiment, the invention provides a method for treating or lessening the severity of a GSK3-mediated disease or condition in a patient comprising the step of administering to said patient a composition according to the present invention.

The term "GSK3-mediated disease" or "GSK3-mediated condition", as used herein, means any disease or other deleterious condition in which GSK3 protein kinase is known to play a role. Such conditions include, without limitation, diabetes, neurodegenerative disorders, Alzheimer's disease, Huntington's, Parkinson's, AIDS associated dementia, amyotrophic lateral sclerosis (AML), multiple sclerosis (MS), schizophrenia, stroke, cardiomycete hypertrophy, and baldness.

According to another embodiment, the invention provides a method for treating or lessening the severity of an Aurora2-mediated disease or condition in a patient comprising the step of administering to said patient a composition according to the present invention.

The term "Aurora2-mediated disease" or "Aurora2-mediated condition", as used herein, means any disease or other deleterious condition in which Aurora2 protein kinase is known to play a role. Such conditions include, without limitation, cancers such as colon and breast cancer.

According to another embodiment, the invention provides a method for treating or lessening the severity of a Syk-mediated disease or condition in a patient comprising the step of administering to said patient a composition according to the present invention.

The term "Syk-mediated disease" or "Syk-mediated condition", as used herein, means any disease or other deleterious condition in which Syk protein kinase is known to play a role. Such conditions include, without limitation, allergic disorders, especially asthma.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

In order that the invention described herein may be more fully understood, the following examples are set forth. It should be understood that these examples are for illustrative purposes only and are not to be construed as limiting this invention in any manner.

EXAMPLES

Example 1

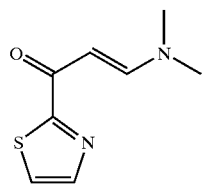

3-Dimethylamino-1-thiazol-2-yl-propenone (2):

To a solution of 2-acetylthiazole (500 mg, 3.93 mmol) in 2 mL of THF was added dimethylformamide-dimethylacetal (1.6 ml, 7.86 mmol) and the resulting solution was stirred at room temperature overnight. The reaction mixture was evaporated and the residue triturated with ethyl acetate and the product isolated by filtration. The filtered solid was washed with diethyl ether and dried to afford 2 (400 mg) as a yellow solid.

Example 2

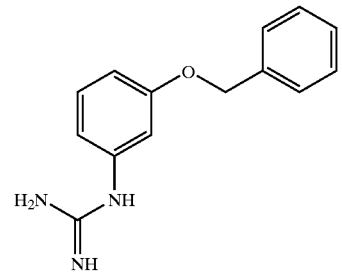

N-(3-Benzyloxy-phenyl)-guanidine (4):

3-benzyloxy aniline (1 g, 5 mmol) and cyanamide (420 mg, 10 mmol) were dissolved in 4 mL of 4N HCl in dioxane and heated to 120° C. overnight. The reaction mixture was cooled to room temperature, quenched with water, and extracted with diethyl ether. The aqueous layer was made basic with 2N NaOH and extracted thrice with dichloromethane. The organic extracts were combined and washed with brine, dried over $MgSO_4$, and concentrated to afford 4 (450 mg) as a light brown solid.

Example 3

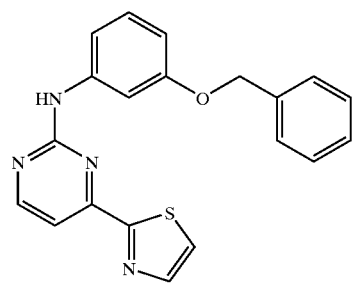

(3-Benzyloxy-phenyl)-(4-thiazol-2-yl-pyrimidin-2-yl)-amine (I-7):

A solution of 3-benzyloxy guanidine 4 (50 mg, 0.20 mmol) and enaminone 2 (50 mg, 0.27 mmol) in ethanol (3 mL) was heated at reflux in a sealed tube overnight. The reaction mixture was concentrated and the residue purified by column chromatography to afford compound I-7 (20 mg). M+1 (obs) 347.1. $R_t$=4.28 minutes.

Example 4

We have prepared other compounds of formula I by methods substantially similar to those described in the above Examples 1–3 and those illustrated in Scheme I. The characterization data for these compounds is summarized in Table 3 below and includes LC/MS (M+1 observed), HPLC, and ¹HNMR data.

The term "$R_t$(min)" refers to the retention time, in minutes, associated with the compound using the following HPLC method. The $R_t$ was determined using a Waters ODS-AQ (2×50 mm) column at ambient temperature with a gradient of 10→90% $CH_3CN$ in water over 5 minutes and with the absorbance detected as an average of 190–380 nM@4 nM increments.

The term "Y" designates that ¹HNMR data was obtained and found to be consistant with the assigned structure.

Compound numbers correspond to the compound numbers listed in Table 1.

TABLE 3

Characterization Data for Selected Compounds of Formula I

| Compound No | M + 1 (obs) | R$_t$(min) | $^1$H NMR |
|---|---|---|---|
| I-16 | 300.0 | 3.15 | — |
| I-19 | 273.0 | 3.18 | — |
| I-22 | 289.0 | 3.47 | — |
| I-28 | 290.0 | 2.76 | — |
| I-31 | 381.0 | 3.66 | — |
| I-34 | 334.8 | 3.54 | — |
| I-37 | 323.0 | 3.56 | — |
| I-40 | 300.0 | 3.19 | — |
| I-43 | 273.0 | 3.1 | — |
| I-46 | 289.0 | 3.19 | — |
| I-49 | 291.0 | 3.33 | — |
| I-52 | 305.0 | 3.62 | — |
| I-55 | 334.0 | 2.16 | — |
| I-58 | 309.0 | 3.60 | — |
| I-61 | 322.9 | 2.99 | — |
| I-64 | 291.0 | 2.67 | — |
| I-67 | 269.0 | 3.28 | — |
| I-73 | 283.0 | 3.53 | — |
| I-10 | 361.1 | 3.76 | — |
| I-13 | 347.0 | 3.82 | — |
| I-4 | 347.1 | 4.14 | — |
| I-7 | 361.1 | 4.28 | — |
| I-25 | 285.0 | 2.98 | — |
| I-76 | 367.2 | 4.53 | — |
| I-79 | 386.1 | 3.58 | — |
| I-82 | 419.1 | 3.80 | — |
| I-85 | 397.1 | 3.94 | — |
| I-88 | 395.1 | 4.11 | — |
| I-100 | 379.1 | 3.85 | — |
| I-103 | 397.1 | 3.98 | — |
| I-106 | 429.1 | 4.13 | — |
| I-109 | 379.1 | 3.84 | — |
| I-112 | 429.0 | 4.40 | — |
| I-115 | 375.2 | 3.96 | — |
| I-2 | 429.0 | 4.38 | — |
| I-5 | 439.1 | 3.24 | — |
| I-8 | 362.1 | 2.21 | — |
| I-11 | — | — | Y |
| I-14 | 376.2 | 2.56 | — |
| I-17 | 405.1 | 3.72 | — |
| I-20 | 362.1 | 2.54 | — |
| I-23 | 362.1 | 2.55 | — |
| I-29 | 364.2 | 3.52 | — |
| I-35 | 406.1 | 3.8 | Y |
| I-38 | 376.1 | 3.13 | Y |
| I-41 | 379.2 | 3.84 | — |
| I-44 | 391.1 | 3.84 | — |
| I-47 | 429.1 | 4.12 | — |
| I-91 | 429.1 | 4.12 | — |
| I-94 | 397.1 | 3.75 | — |

Example 5

GSK-3 Inhibition Assay

Compounds were screened for their ability to inhibit GSK3-β (AA 1–420) activity using a standard coupled enzyme system (Fox et al. (1998) *Protein Sci.* 7, 2249). Reactions were carried out in a solution containing 100 mM HEPES (pH 7.5), 10 mM MgCl$_2$, 25 mM NaCl, 300 μM NADH, 1 mM DTT and 1.5% DMSO. Final substrate concentrations in the assay were 10 μM ATP (Sigma Chemicals, St Louis, Mo.) and 300 μM peptide (HSSPHQS (PO$_3$H$_2$)EDEEE, American Peptide, Sunnyvale, Calif.). Reactions were carried out at 30° C. and 60 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. 59 μl of the test reaction was placed in a 96 well ½-diameter plate (Corning, Corning, N.Y.) then treated with 1 μl of a 2 mM DMSO stock containing the test compound (final compound concentration 30 μM). The plate was incubated for ~10 minutes at 30° C. then the reaction initiated by addition of 7 μl of ATP (final concentration 10 μM). Rates of reaction were obtained using a Molecular Devices Spectramax plate reader (Sunnyvale, Calif.) over a 5 minute read time at 30° C. Compounds showing greater than 50% inhibition versus standard wells containing DMSO, but no compound, were titrated and K$_i$ values were determined.

Table 4 shows the results of the activity of selected compounds of this invention in the GSK3 inhibition assay. The compound numbers correspond to the compound numbers in Table 1. Compounds having a K$_i$ less than 0.1 micromolar (μM) are rated "A", compounds having a K$_i$ between 0.1 and 1 μM are rated "B" and compounds having a K$_i$ greater than 1 μM are rated "C".

TABLE 4

GSK3-β Activity of Selected Compounds

| No. I- | Activity | No. I- | Activity | No. I- | Activity |
|---|---|---|---|---|---|
| 16 | C | 19 | A | 22 | A |
| 28 | A | 31 | A | 34 | A |
| 37 | A | 40 | A | 43 | A |
| 46 | A | 49 | A | 52 | A |
| 55 | A | 58 | A | 61 | C |
| 64 | C | 67 | B | 73 | A |
| 10 | C | 4 | A | 7 | — |
| 25 | A | 76 | A | 79 | A |
| 82 | A | 85 | A | 88 | A |
| 100 | A | 103 | A | 106 | A |
| 109 | A | 112 | A | 115 | A |
| 2 | C | 5 | A | 8 | A |
| 11 | A | 14 | A | 17 | A |
| 20 | A | 23 | A | 29 | A |
| 35 | A | 38 | A | 41 | A |
| 44 | A | 47 | A | 91 | A |
| 94 | A | 3 | A | 6 | A |
| 9 | A | 12 | A | 15 | A |
| 18 | A | 21 | C | 24 | A |
| 27 | A | 30 | A | 33 | A |
| 36 | B | 39 | A | 42 | A |
| 45 | A | 48 | A | 51 | B |
| 54 | A | 57 | A | 60 | A |
| 63 | A | 66 | A | 69 | A |
| 72 | A | 75 | A | 78 | A |
| 81 | A | 84 | A | 87 | A |
| 90 | A | 93 | C | 96 | C |
| 99 | A | — | — | 105 | A |
| 108 | B | 111 | A | 114 | C |
| 117 | C | — | — | — | — |

Example 6

Aurora2 Inhibition Assay

Compounds are screened in the following manner for their ability to inhibit Aurora2 using a standard coupled enzyme assay (Fox et al (1998) *Protein Sci* 7, 2249). To an assay stock buffer solution containing 0.1M HEPES 7.5, 10 mM MgCl$_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 μM peptide (LRRASLG, American Peptide, Sunnyvale, Calif.) is added a DMSO solution of a compound of the present invention to a final concentration of 30 μM. The resulting mixture is incubated at 30° C. for 10 minutes. The reaction was initiated by the addition of 10 μL of Aurora2 stock solution to give a final concentration of 70 nM in the assay. The rates of reaction are obtained by monitoring absorbance at 340 nm over a 5 minute read time at 30° C. using a BioRad Ultramark plate reader (Hercules, Calif.). The $IC_{50}$ values are determined from the rate data as a function of inhibitor concentration.

Table 5 shows the results of the activity of selected compounds of this invention in the Aurora2 inhibition assay. The compound numbers correspond to the compound numbers in Table 1. Compounds having an $IC_{50}$ less than 0.5 micromolar (μM) are rated "A", compounds having an $IC_{50}$ between 0.5 and 2 μM are rated "B" and compounds having an $IC_{50}$ greater than 2 μM are rated "C".

TABLE 5

Aurora2 Activity of Selected Compounds

| No. I- | Activity | No. I- | Activity | No. I- | Activity |
|---|---|---|---|---|---|
| 2 | C | 4 | B | 5 | C |
| 7 | C | 8 | A | 10 | C |
| 11 | A | 13 | C | 14 | B |
| 16 | A | 17 | A | 19 | B |
| 20 | A | 22 | A | 23 | A |
| 25 | B | 26 | A | 28 | C |
| 29 | A | 31 | A | — | — |
| 34 | A | 35 | C | 37 | B |
| 38 | A | 40 | C | 41 | C |
| 43 | C | 46 | C | 49 | B |
| 50 | B | 52 | C | 55 | A |
| 56 | B | 58 | C | 59 | C |
| 61 | C | 62 | B | 64 | C |
| 67 | A | 70 | B | 73 | A |
| 76 | C | 79 | C | 82 | C |
| 85 | C | 88 | B | 91 | C |
| 94 | A | 97 | C | 100 | C |
| 103 | C | 106 | C | 109 | C |
| 112 | C | 114 | B | — | — |

Example 7

Syk Inhibition Assay

Compounds were screened for their ability to inhibit Syk using a standard coupled enzyme assay (Fox et al (1998) Protein Sci 7, 2249). Reactions were carried out in 100 mM HEPES pH 7.5, 10 mM $MgCl_2$, 25 mM NaCl, 1 mM DTT and 1.5% DMSO. Final substrate concentrations in the assay were 200 μM ATP (Sigma chemical Co.) and 4 μM poly Gly-Tyr peptide (Sigma Chemical Co.). Assays were carried out at 30° C. and 200 nM Syk. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above, with the exception of Syk, DTT and the test compound of interest. 56 μl of the test reaction was placed in a 96 well plate followed by the addition of 1 μl of 2 mM DMSO stock containing the test compound (final compound concentration 30 μM). The plate was pre-incubated for ~10 minutes at 30° C. and the reaction initiated by the addition of 10 μl of enzyme (final concentration 25 nM). Rates of reaction were obtained using a BioRad Ultramark plate reader (Hercules, Calif.) over a 5 minute read time at 30° C. Compounds showing >50% inhibition versus standard wells containing DMSO, but no compound, were titrated and IC50's determined using a similar protocol.

Table 6 shows the results of the activity of selected compounds of this invention in the Syk inhibition assay. The compound numbers correspond to the compound numbers in Table 1. Compounds having an $IC_{50}$ less than 0.5 micromolar (μM) are rated "A", compounds having an $IC_{50}$ between 0.5 and 2 μM are rated "B" and compounds having an $IC_{50}$ greater than 2 μM are rated "C".

TABLE 6

Syk Activity of Selected Compounds

| No. I- | Activity | No. I- | Activity | No. I- | Activity |
|---|---|---|---|---|---|
| 2 | C | 4 | B | 5 | A |
| 7 | A | 8 | C | 11 | A |
| 14 | B | 16 | B | 17 | A |
| 19 | B | 22 | A | 23 | A |
| 25 | A | 29 | A | 31 | A |
| 34 | A | 35 | C | 37 | A |
| 38 | A | 43 | C | 44 | A |
| 46 | C | 47 | C | 49 | C |
| 50 | A | 52 | C | 53 | B |
| 55 | A | 56 | B | 58 | C |
| 59 | C | 61 | C | 62 | A |
| 64 | C | 67 | A | 73 | A |
| 76 | C | 82 | C | 88 | C |
| 91 | C | 94 | A | 106 | C |
| 109 | C | 112 | C | 115 | C |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I:

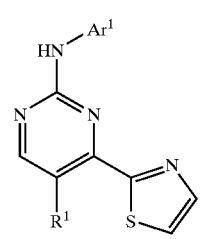

I or a pharmaceutically acceptable derivative thereof, wherein;

$R^1$ is selected from R, halogen, CN, $NO_2$, or TR;

T is an optionally substituted $C_1$–$C_4$ alkylidene chain wherein up to two methylene units of T are optionally and independently replaced by O, N(R), C(O), S, SO, or $SO_2$;

each R is independently selected from hydrogen or an optionally substituted $C_{1-6}$ aliphatic group, wherein:
 two R bound to the same nitrogen atom are optionally taken together with the nitrogen to form a 3–7 membered saturated, partially unsaturated, or fully unsaturated ring having 0–2 heteroatoms, in addition to the nitrogen bound thereto, independently selected from nitrogen, oxygen, or sulfur;

$Ar^1$ is an optionally substituted phenyl ring wherein:
 $Ar^1$ is optionally substituted by one to four substituents selected from the group consisting of:
  (a) one group selected from QR, $Ar^2$, or $QAr^2$; and (b) up to four $R^2$ groups;

each Q is independently selected from a valence bond or an optionally substituted $C_{1-6}$ alkylidene chain, wherein:
one or two non-adjacent methylene units of Q are optionally and independently replaced by —O—, —S—, —NR—, —C(O)—, —CO$_2$—, —C(O)NR—, —OC(O)NR—, —C(O)C(O)—, —NRC(O)—, NRCO$_2$—, —NRC(O)NR—, —S(O)—, —SO$_2$—, —NRSO$_2$—, —SO$_2$NR—, or —NRSO$_2$R—;

each $Ar^2$ is an optionally substituted ring independently selected from:
(a) a 3–8 membered monocyclic or 8–10 membered bicyclic saturated, partially unsaturated, or aryl ring;
(b) a 3–7 membered heterocyclic ring having 1–3 heteroatoms independently selected from nitrogen, oxygen, or sulfur; or
(c) a 5–6 membered monocyclic or 8–10 bicyclic heteroaryl ring having 1–4 heteroatoms dependently selected from nitrogen, oxygen, or sulfur, wherein:
$Ar^2$ is optionally substituted by one to four $R^2$ groups; and each $R^2$ is independently selected from R, halogen, NO$_2$, CN, OR, SR, N(R)$_2$, NRCOR, NRCON(R)$_2$, NRCO$_2$R, C(O)R, CO$_2$R, CON(R)$_2$, OC(O)N(R)$_2$, SOR, SO$_2$R, SO$_2$N(R)$_2$, NRSO$_2$R, NRSO$_2$N(R)$_2$, C(O)C(O)R, or C(O)CH$_2$C(O)R; wherein:
two $R^2$ on adjacent positions on $Ar^1$ or $Ar^2$ are optionally taken together to form a saturated, partially unsaturated, or fully unsaturated 4–6 membered ring having 0–3 heteroatoms independently selected from nitrogen, oxygen, or sulfur;

provided that:
$R^1$ is other than CN.

2. The compound according to either of claim 1, wherein:
$Ar^1$ is substituted by one to four substituents selected from the group consisting of:
(a) one group selected from QR or QAr$^2$; and
(b) up to four $R^2$ groups; wherein:
each $R^2$ is independently selected from halogen, CN, CO$_2$R, R, NO$_2$, OR, haloalkyl, SO$_2$N(R)$_2$, or N(R)$_2$;
each Q is independently selected from a $C_{1-4}$ alkylidene chain wherein one or two methylene units of Q are optionally replaced by O, NH, NHCO, NHCO$_2$, NHSO$_2$, or CONH; and
$Ar^2$ is is a 3–6 membered carbocyclic ring or an optionally substituted phenyl or 5–6 membered heterocyclic or heteroaryl ring having one to two heteroatoms independently selected from nitrogen, oxygen, or sulfur.

3. The compound according to either of claim 1, wherein:
$Ar^1$ is substituted by $Ar^2$ and optionally substituted with 1–2 $R^2$ substituents, wherein:
each $Ar^2$ is an optionally substituted ring independently selected from:
(a) a phenyl, indanyl, or naphthyl ring;
(b) a 5–6 membered heterocyclic ring having 1–3 heteroatoms independently selected from nitrogen, oxygen, or sulfur; or
(c) a 5–6 membered monocyclic or 9–10 membered bicyclic heteroaryl ring having 1–2 heteroatoms independently selected from oxygen, nitrogen, or sulfur; wherein:
$Ar^2$ is optionally substituted with 1–2 $R^2$ groups; and each $R^2$ is independently selected from R, halogen, NO$_2$, CN, OR, SR, N(R)$_2$, C(O)R, SO$_2$N(R)$_2$, or SO$_2$R.

4. A compound selected from the group consisting of:

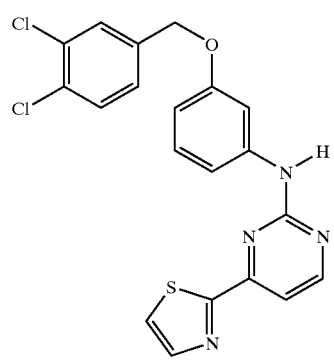

I-2

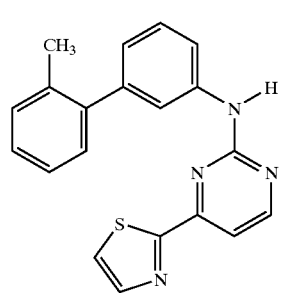

I-3

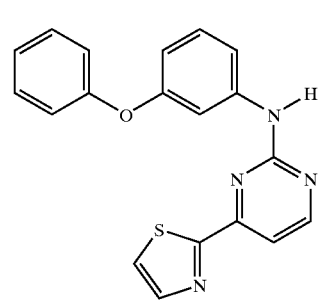

I-4

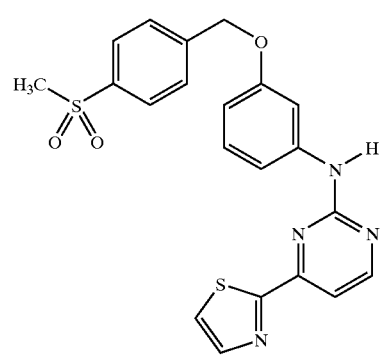

I-5

-continued
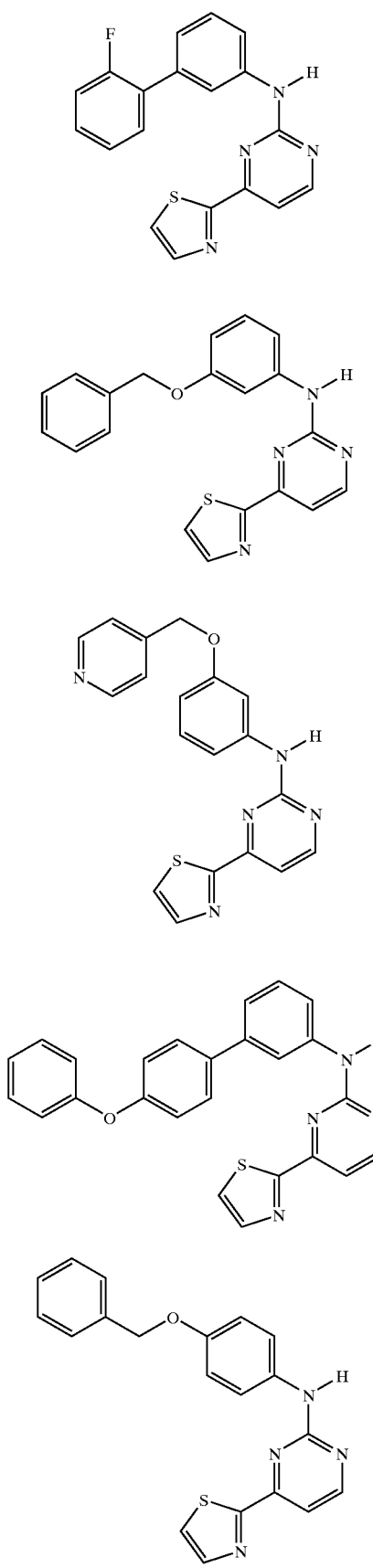
I-6
I-7
I-8
I-9
I-10
-continued
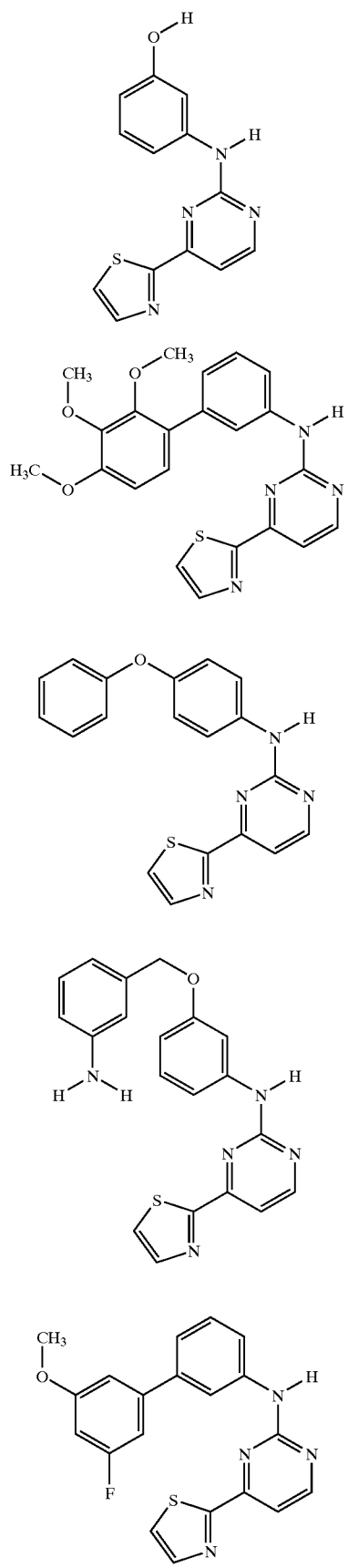
I-11
I-12
I-13
I-14
I-15

-continued
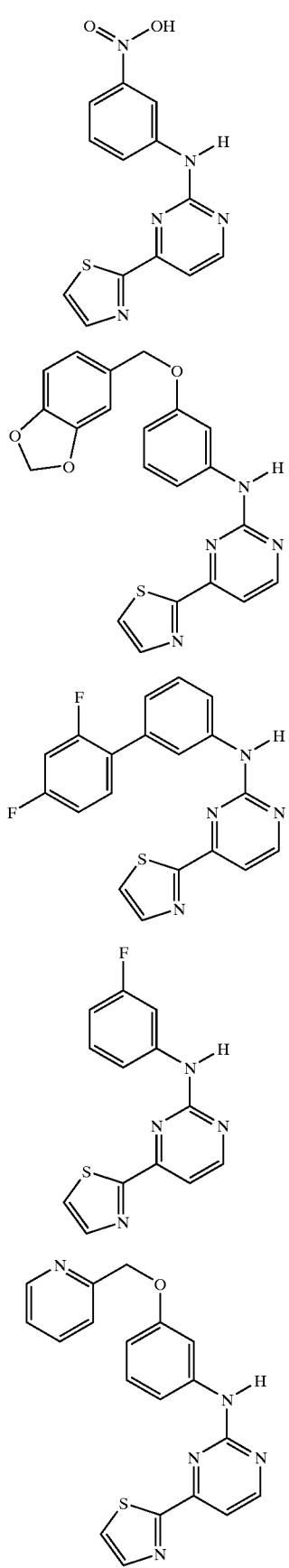
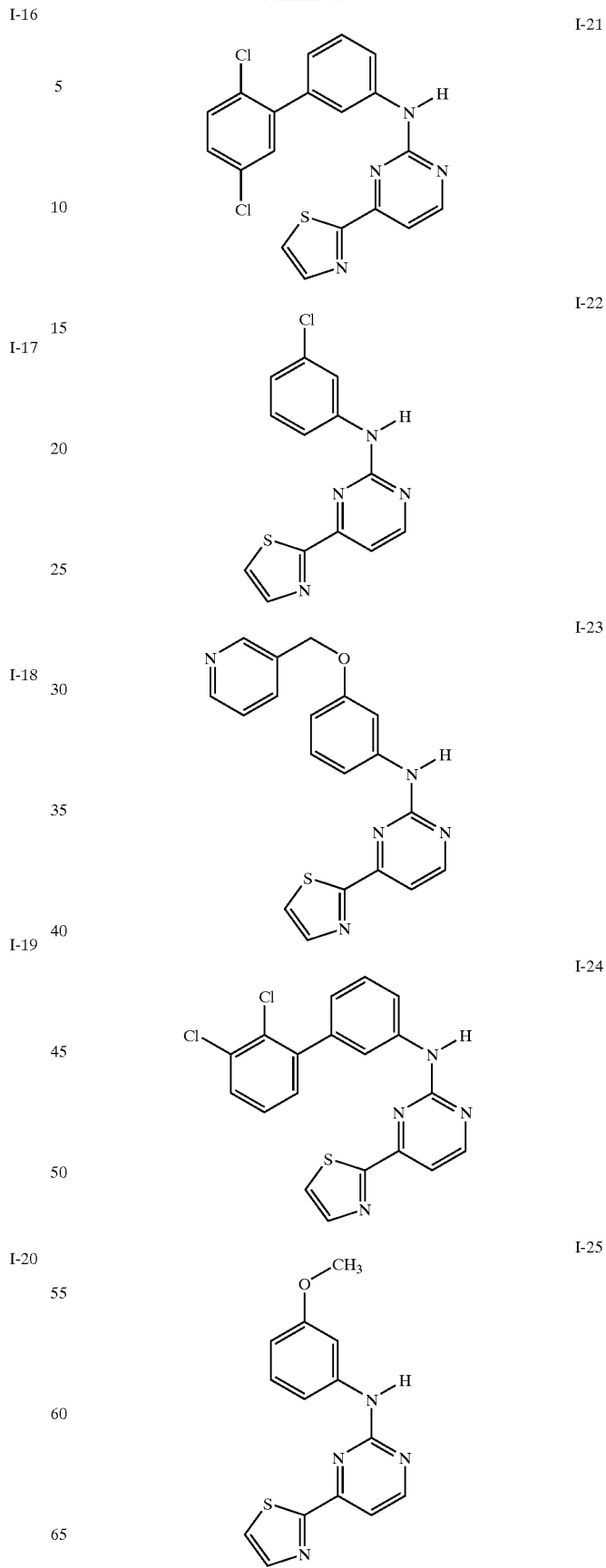

I-26
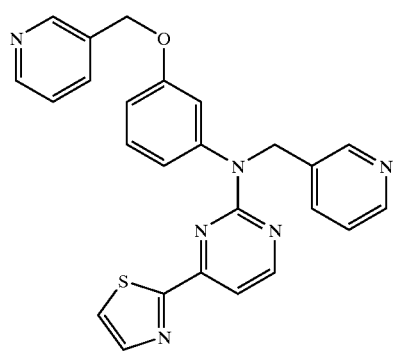
I-27
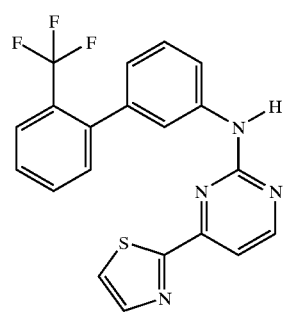
I-28
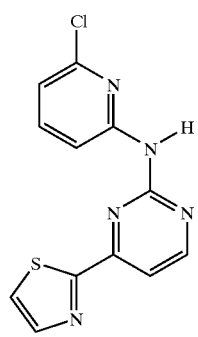
I-29
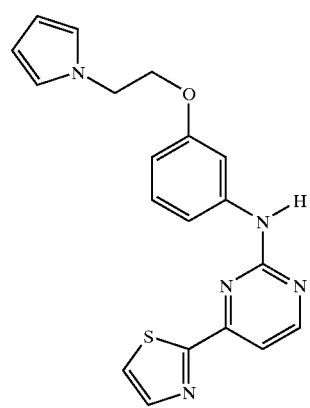
I-30
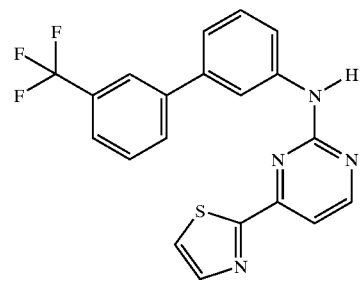
I-31
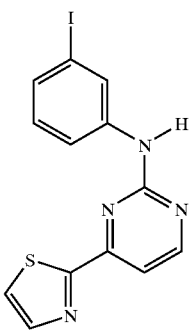
I-33
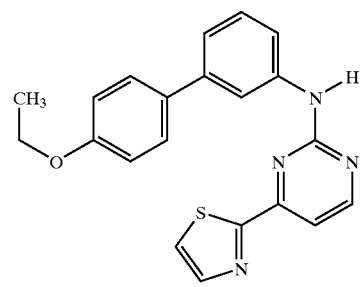
I-34
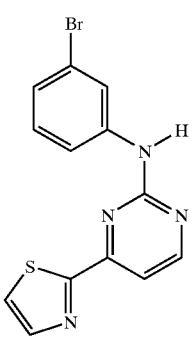
I-35
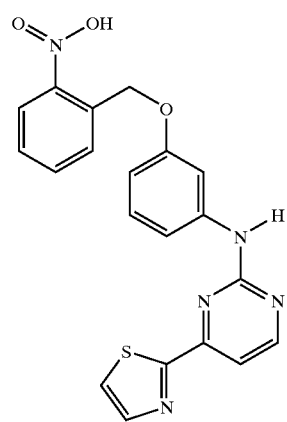

I-36
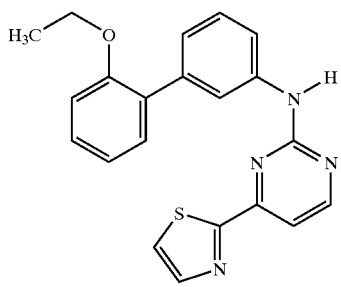
I-37
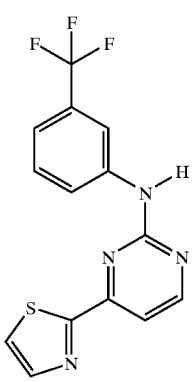
I-38
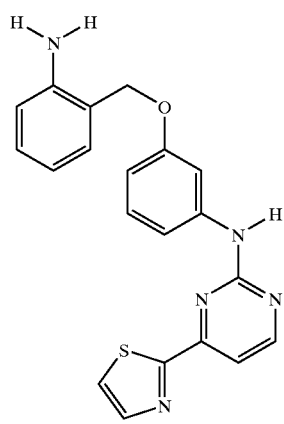
I-39
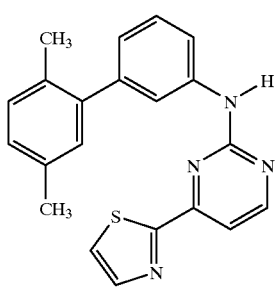
I-40
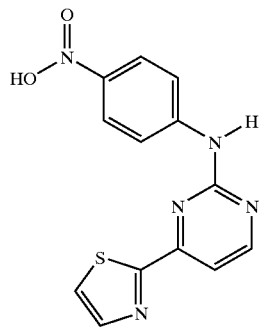
I-41
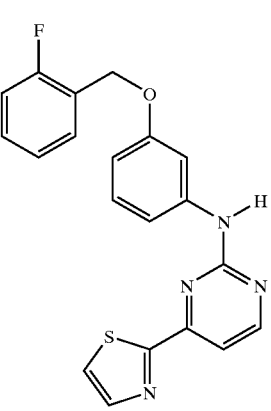
I-42
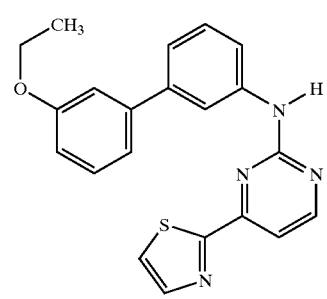
I-43
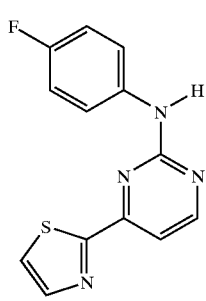

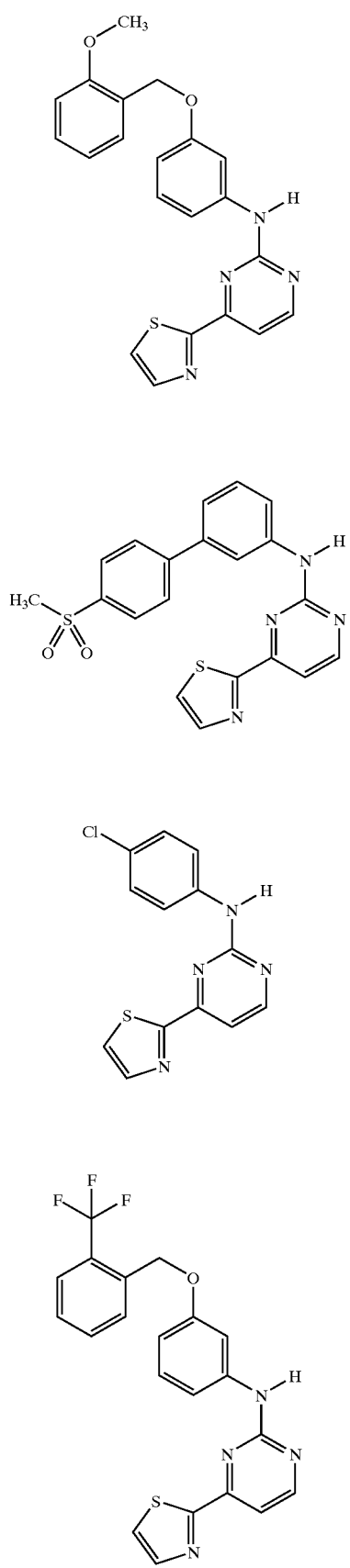
I-44
I-45
I-46
I-47
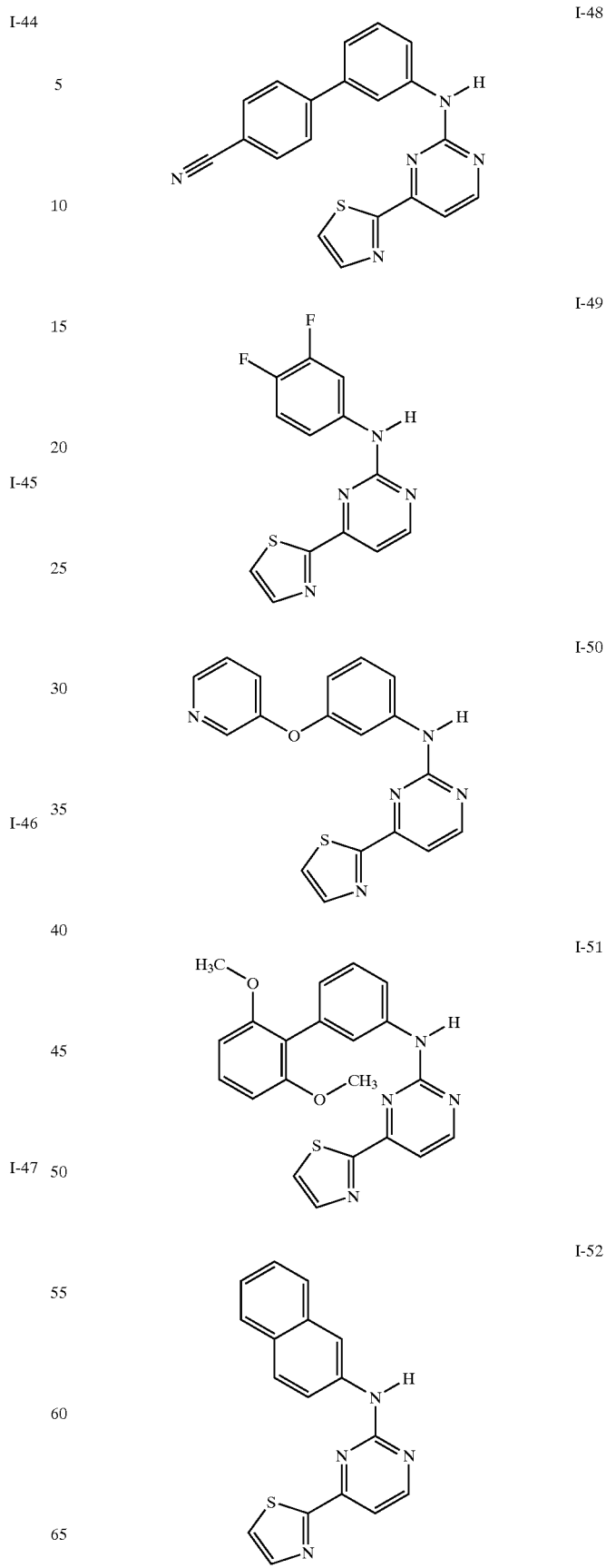
I-48
I-49
I-50
I-51
I-52

I-53
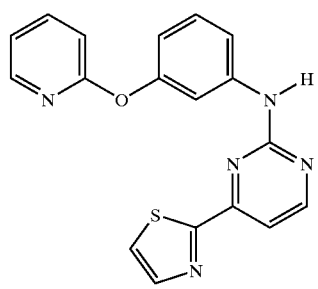
I-54
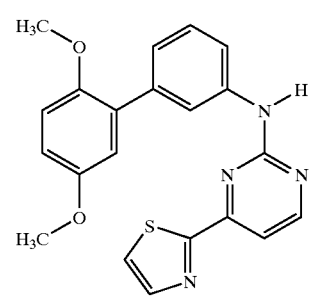
I-55
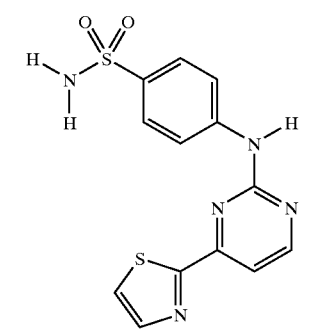
I-56
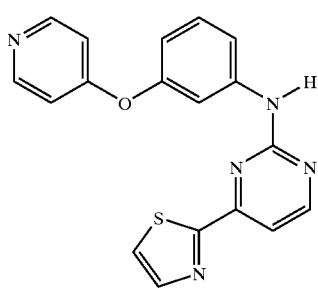
I-57
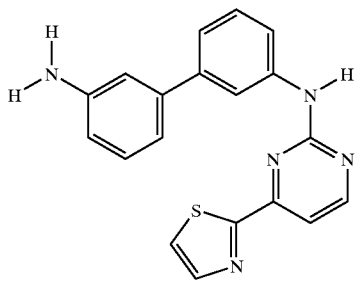
I-58
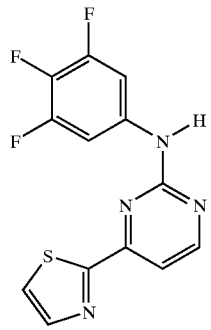
I-59
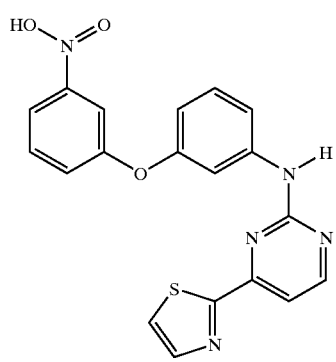
I-60
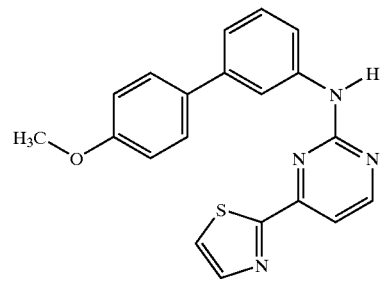
I-61
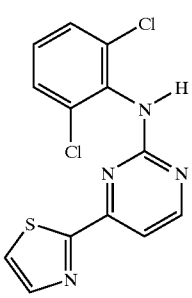
I-62
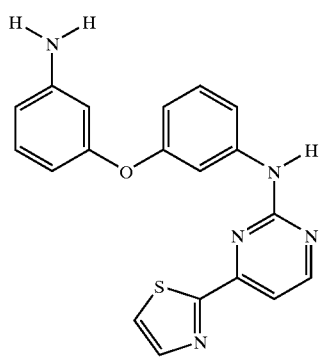

-continued

I-63
I-64
I-65
I-66
I-67

-continued

I-68
I-69
I-70
I-71
I-72

I-73
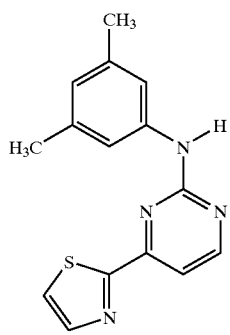
I-74
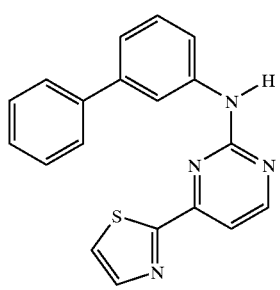
I-75
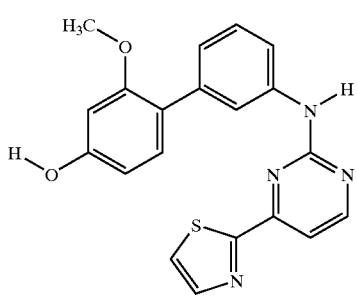
I-76
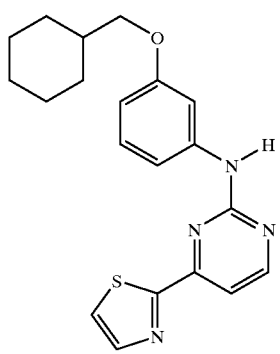
I-77
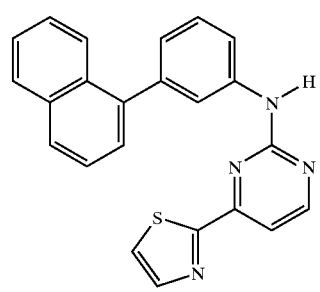
I-78
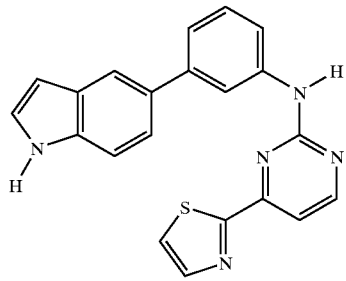
I-79
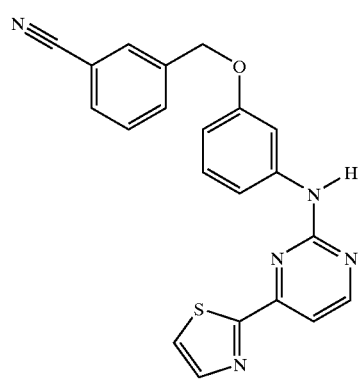
I-80
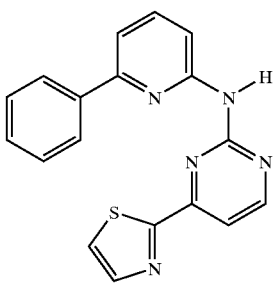
I-81
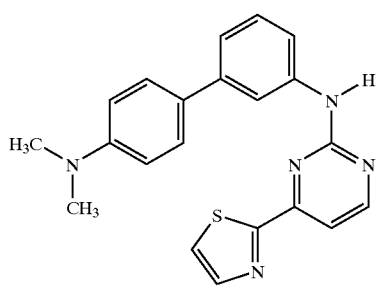
I-82
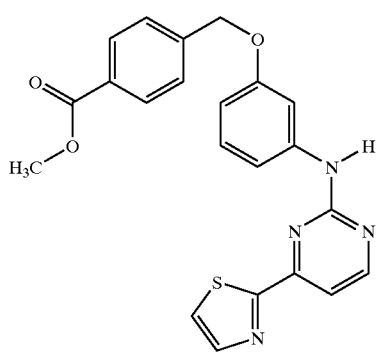

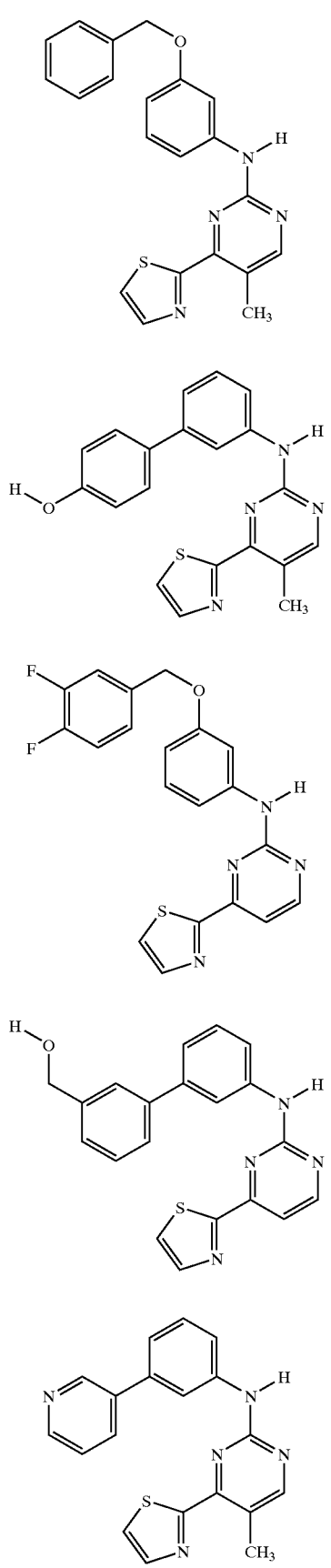

-continued
I-92
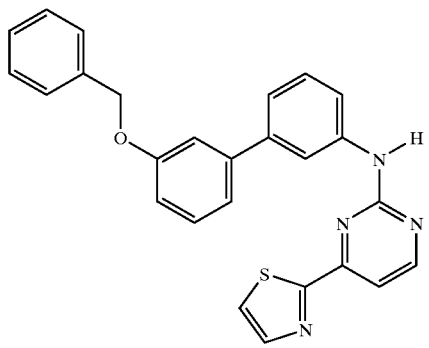
I-93
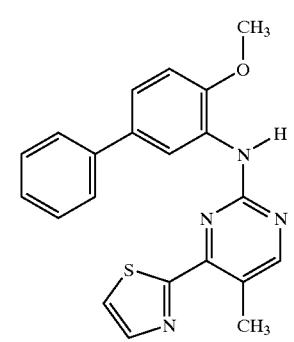
I-94
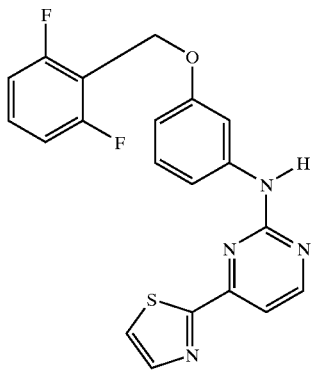
I-95
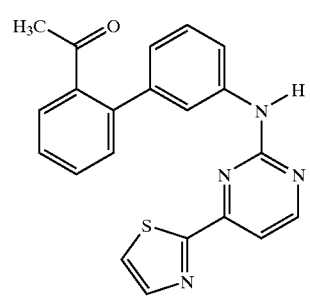
I-96
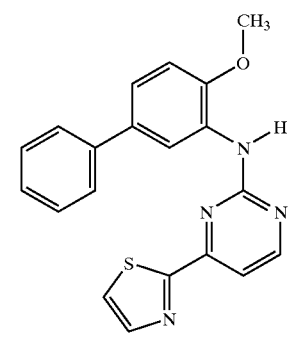
-continued
I-97
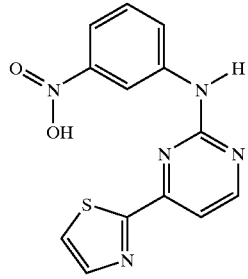
I-98
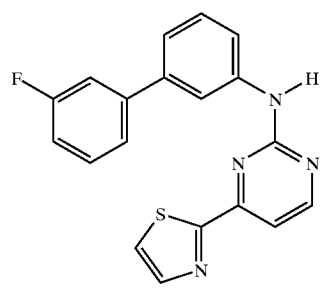
I-99
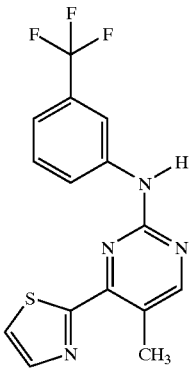
I-100
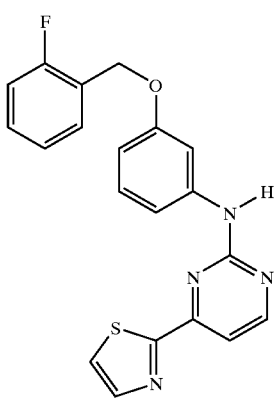
I-101
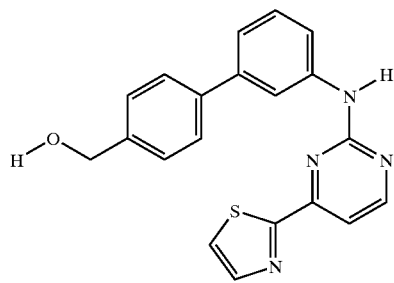

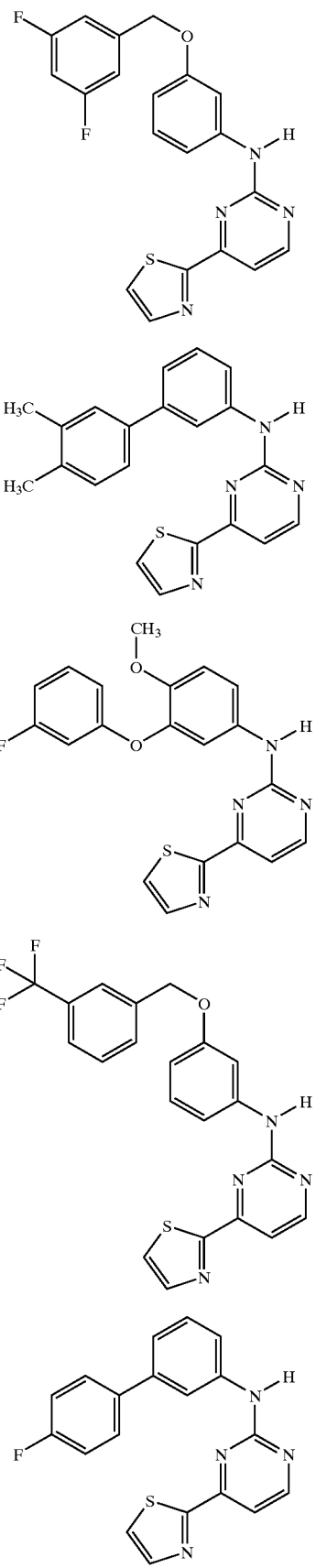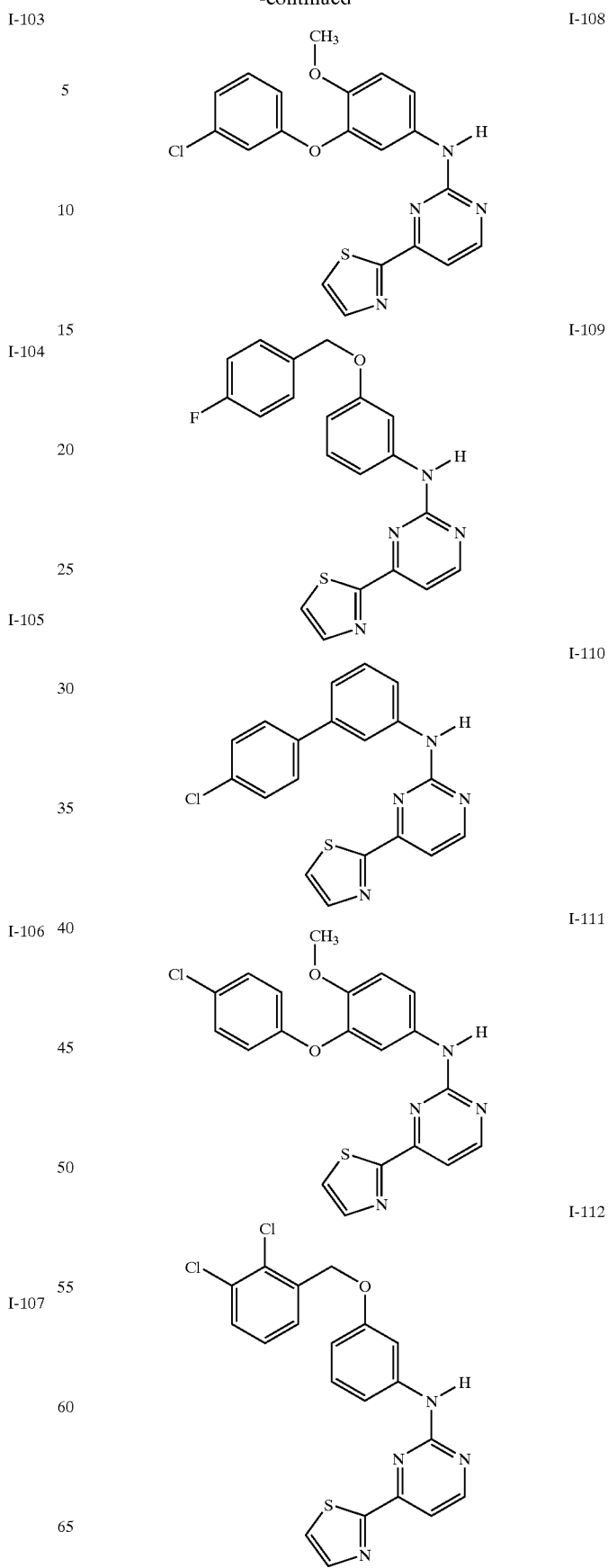

-continued
I-113
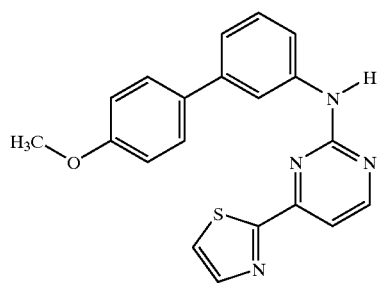
I-114
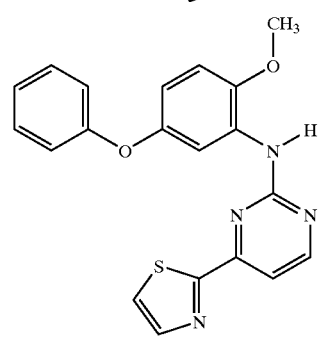
I-115
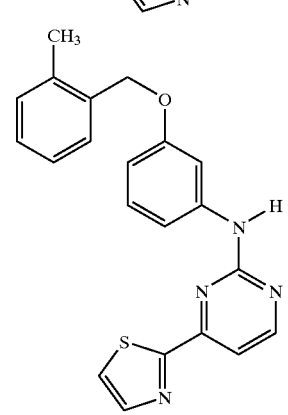
I-116
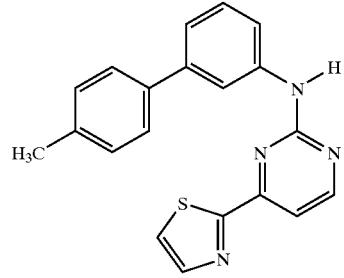
and
I-117
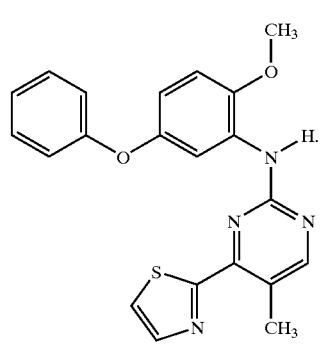
5. A compound selected from the following compounds:
IIa-1
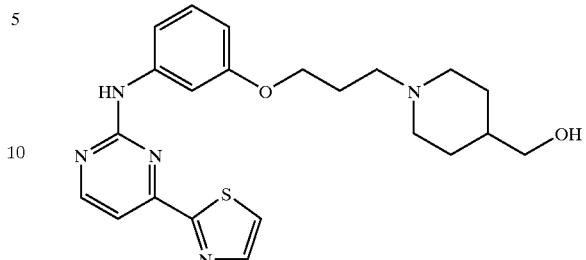
IIa-2
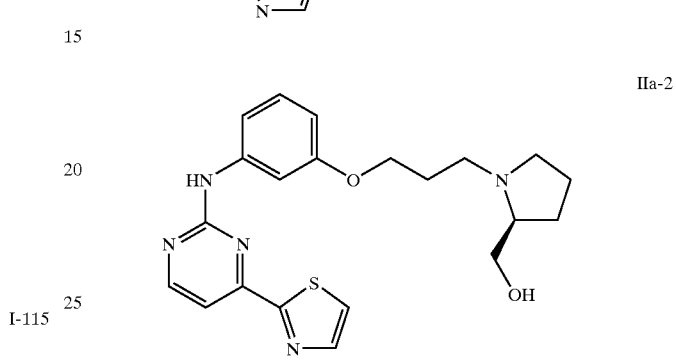
IIa-3
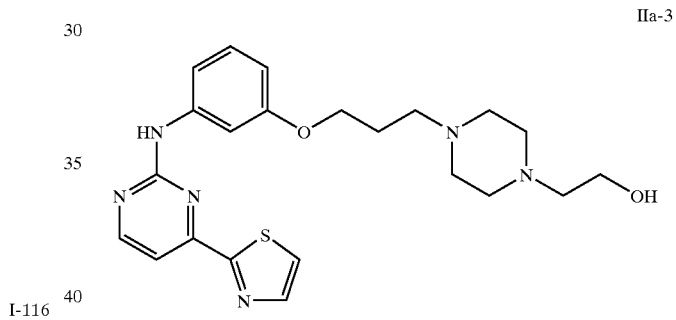
IIa-4
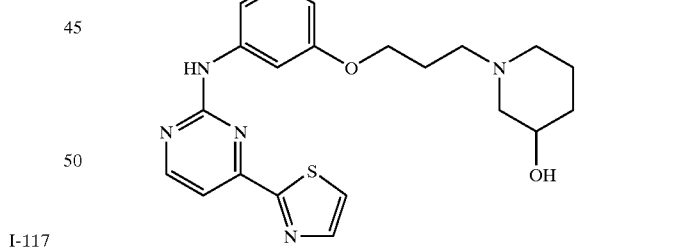
IIa-5
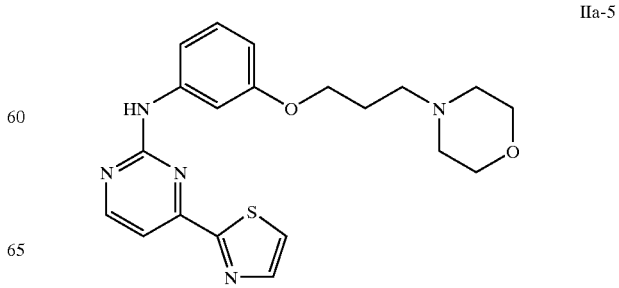

IIa-6
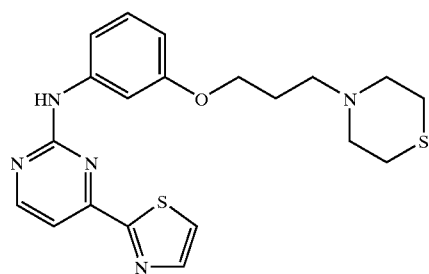
IIa-7
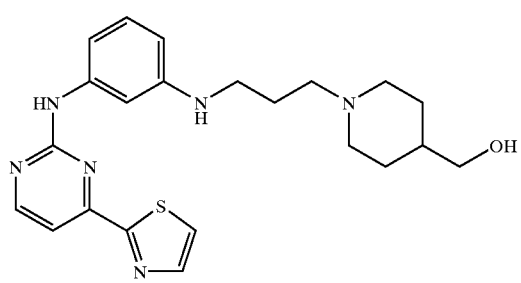
IIa-8
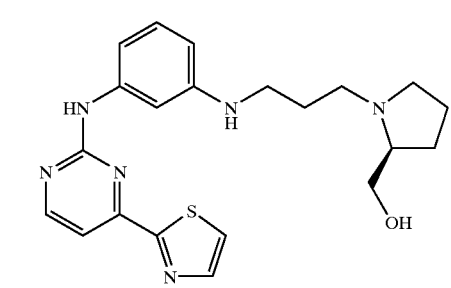
IIa-9
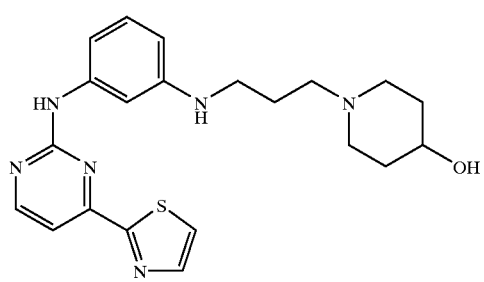
IIa-10
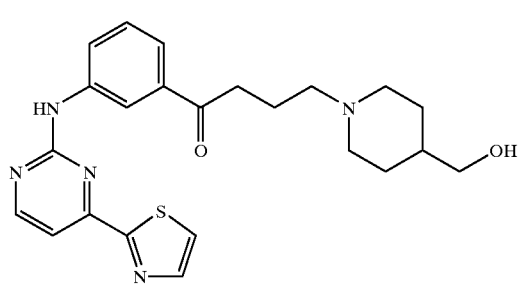
IIa-11
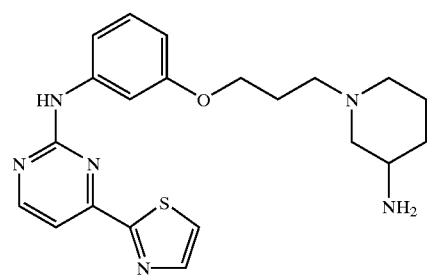
IIa-12
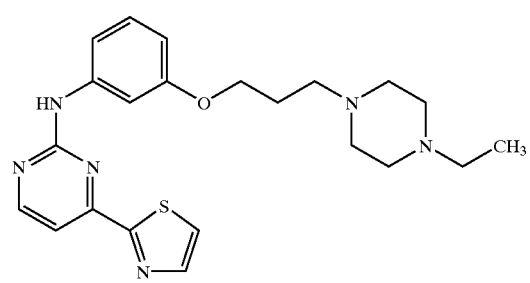
IIa-13
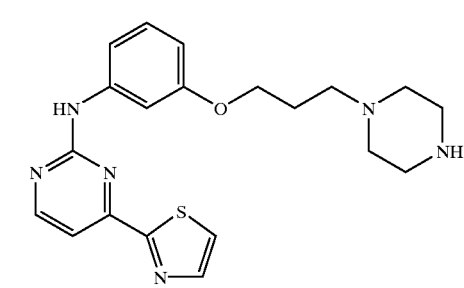
IIa-14
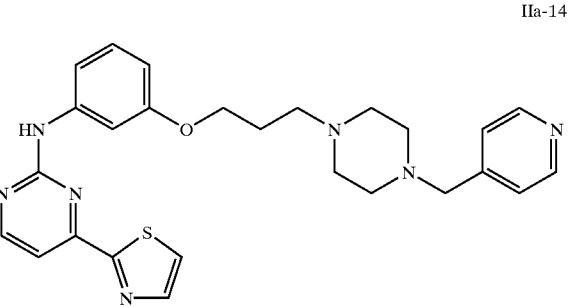
IIa-15
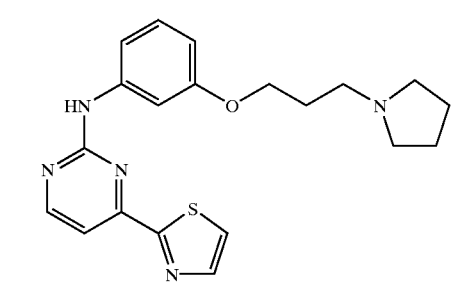

IIa-16 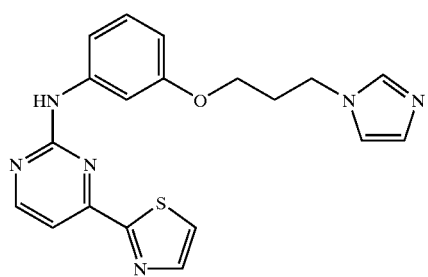
IIa-17 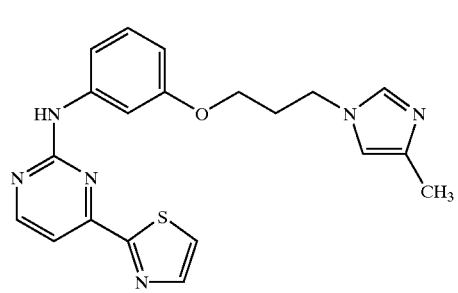
IIa-18 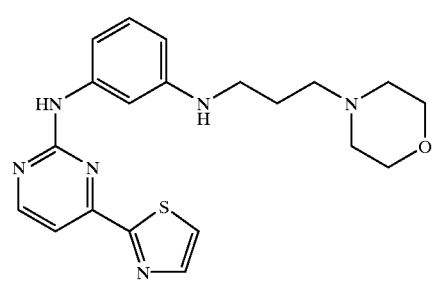
IIa-19 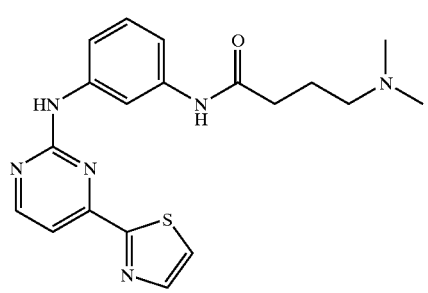
IIa-20 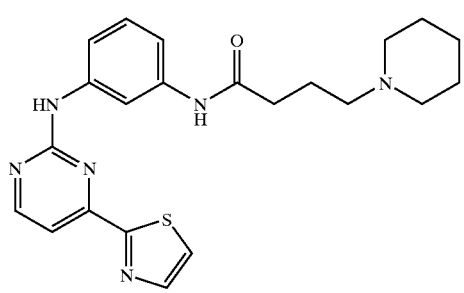
IIa-21 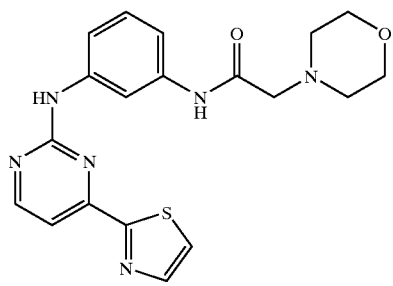
IIa-22 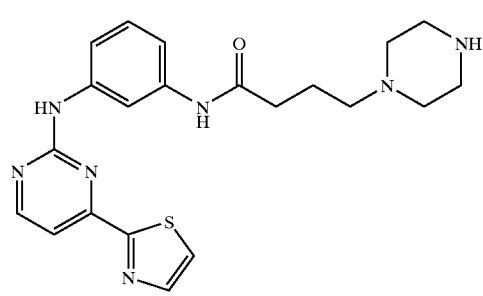
IIa-23 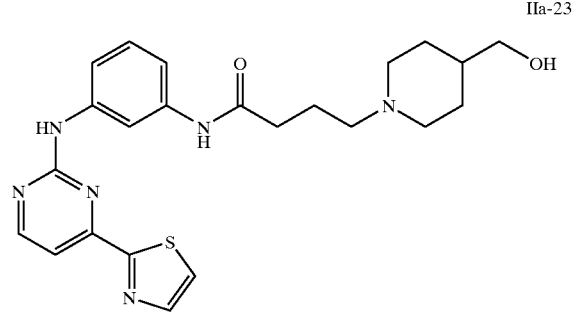
IIa-24 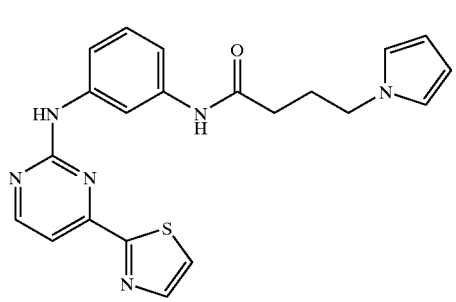
IIa-25 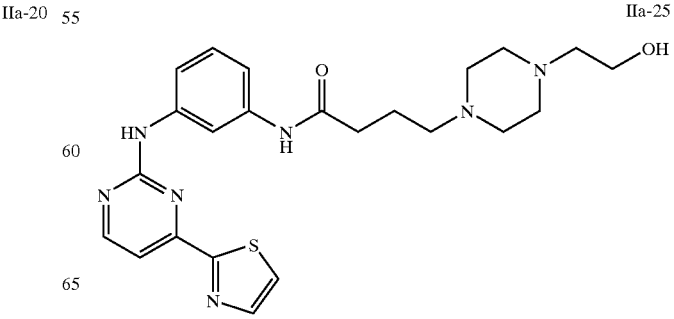

IIa-26 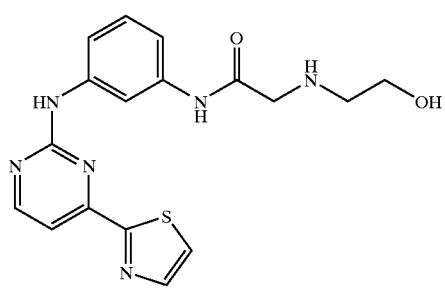
IIa-27 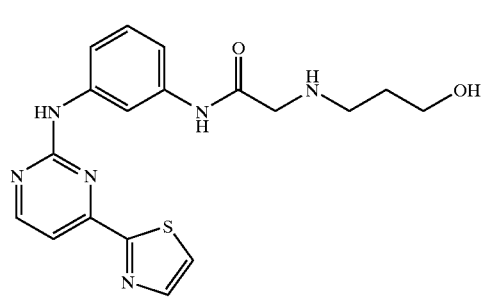
IIa-28 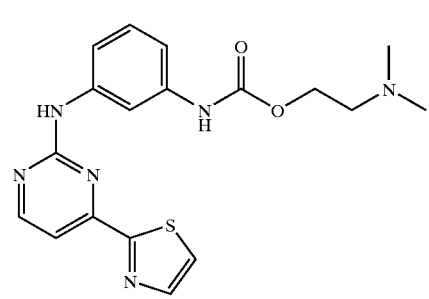
IIa-29 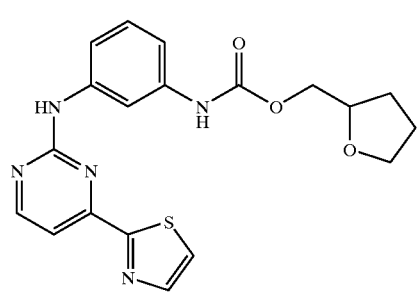
IIa-30 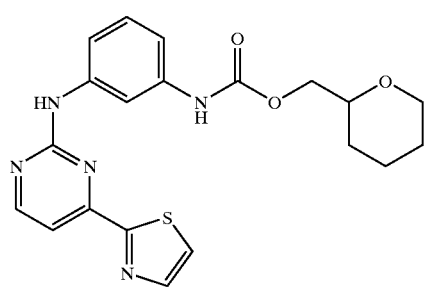
IIa-31 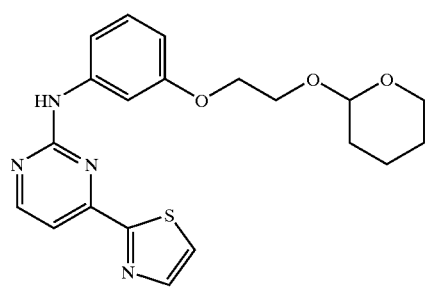
IIa-32 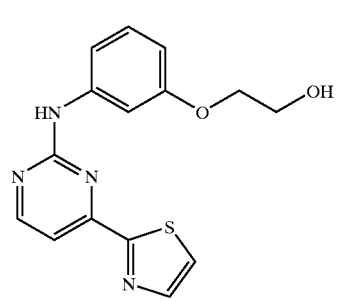
IIa-33 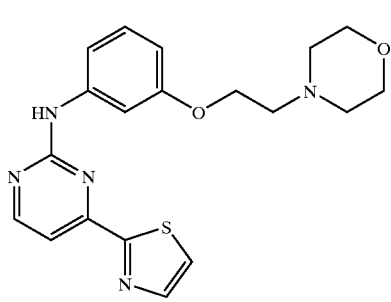
IIa-34 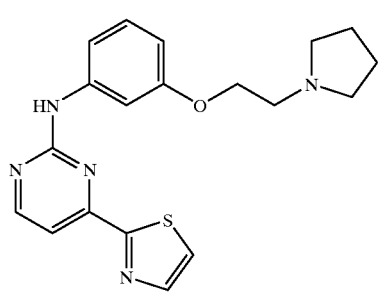
IIa-35 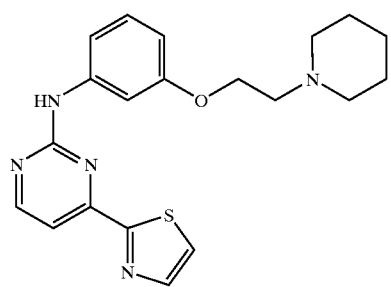

IIa-36
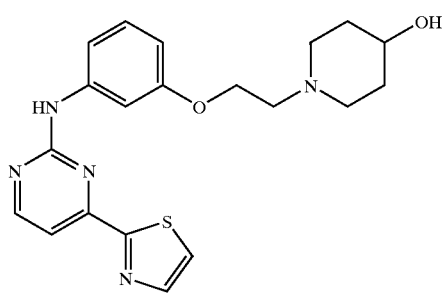
IIa-37
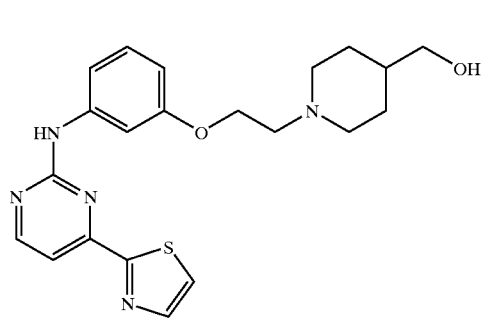
IIa-38
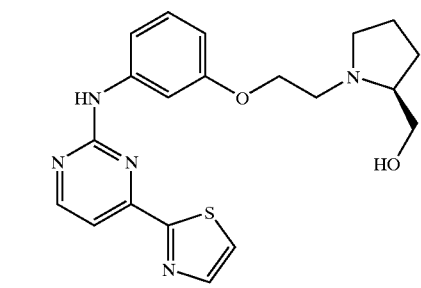
IIa-39
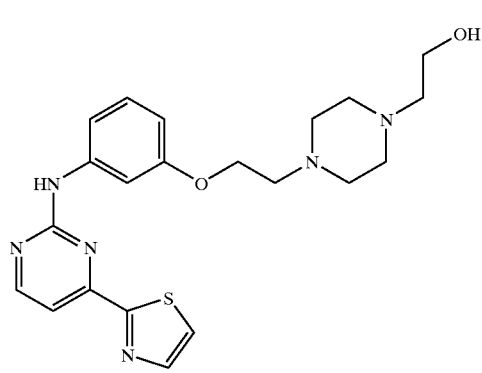
IIa-40
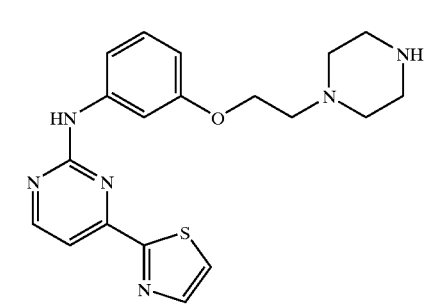
IIa-41
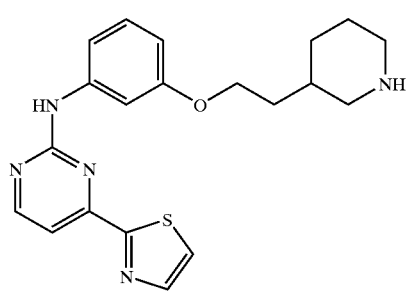
IIa-42
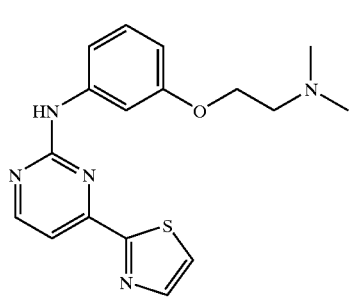
IIa-43
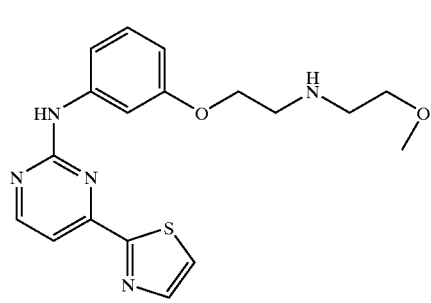
IIa-44
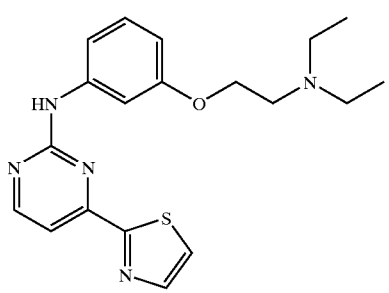
IIa-45
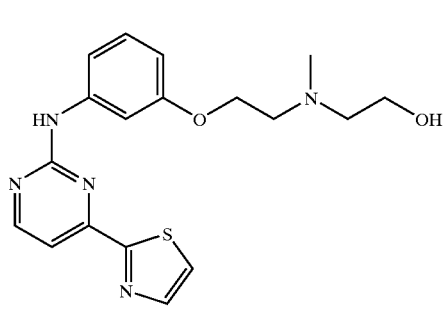

b) a compound of formula I:

I

*structure of formula I shown: HN-Ar¹ attached to pyrimidine bearing R¹ and a thiazole* or a pharmaceutically acceptable derivative thereof, wherein:

$R^1$ is selected from R, halogen, CN, $NO_2$, or TR;

T is an optionally substituted $C_1$–$C_4$ alkylidene chain wherein up to two methylene units of T are optionally and independently replaced by O, N(R), C(O), S, SO, or $SO_2$;

each R is independently selected from hydrogen or an optionally substituted $C_{1-6}$ aliphatic group, wherein:
  two R bound to the same nitrogen atom are optionally taken together with the nitrogen to form a 3–7 membered saturated, partially unsaturated, or fully unsaturated ring having 0–2 heteroatoms, in addition to the nitrogen bound thereto, independently selected from nitrogen, oxygen, or sulfur;

$Ar^1$ is an optionally substituted ring selected from:
  (a) a 3–8 membered monocyclic or 8–10 membered bicyclic saturated, partially unsaturated, or aryl ring;
  (b) a 3–7 membered heterocyclic ring having 1–3 heteroatoms independently selected from nitrogen, oxygen, or sulfur; or
  (c) a 5–6 membered monocyclic or 8–10 membered bicyclic heteroaryl ring having 1–4 heteroatoms independently selected from nitrogen, oxygen, or sulfur, wherein:
    $Ar^1$ is optionally substituted by one to four substituents selected from:
      (a) one group selected from QR, $Ar^2$, or $QAr^2$; and
      (b) up to four $R^2$ groups;

each Q is independently selected from a valence bond or an optionally substituted $C_{1-6}$ alkylidene chain, wherein:
  one or two non-adjacent methylene units of Q are optionally and independently replaced by —O—, —S—, —NR—, —C(O)—, —$CO_2$—, —C(O)NR—, —OC(O)NR—, —C(O)C(O)—, —NRC(O)—, —$NRCO_2$—, —NRC(O)NR—, —S(O)—, —$SO_2$—, —$NRSO_2$—, —$SO_2NR$—, or —$NRSO_2NR$—;

each $Ar^2$ is an optionally substituted ring independently selected from:
  (a) a 3–8 membered monocyclic or 8–10 membered bicyclic saturated, partially unsaturated, or aryl ring;
  (b) a 3–7 membered heterocyclic ring having 1–3 heteroatoms independently selected from nitrogen, oxygen, or sulfur; or
  (c) a 5–6 membered monocyclic or 8–10 membered bicyclic heteroaryl ring having 1–4 heteroatoms independently selected from nitrogen, oxygen, or sulfur, wherein:
    $Ar^2$ is optionally substituted by one to four $R^2$ groups; and 6. A composition comprising a compound according to claim 1, in an amount to detectably inhibit GSK3, Aurora2, or Syk protein kinase activity, and a pharmaceutically acceptable carrier, adjuvant, or vehicle.

7. A method of inhibiting GSK3, Aurora2, or Syk kinase activity in a biological sample, comprising the step of contacting said biological sample with:
  a) a composition according to claim 6; or each $R^2$ is independently selected from R, halogen, $NO_2$, CN, OR, SR, $N(R)_2$, NRCOR, $NRCON(R)_2$, $NRCO_2R$, C(O)R, $CO_2R$, $CON(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$; wherein:

two $R^2$ on adjacent positions on $Ar^1$ or $Ar^2$ are optionally taken together to form a saturated, partially unsaturated, or fully unsaturated 4–6 membered ring having 0–3 heteroatoms independently selected from nitrogen, oxygen, or sulfur.

8. A method of treating a disease in a patient in need thereof, wherein said disease is selected from diabetes, schizophrenia, cardiomycete hypertrophy, a manic depressive disorder, or baldness.

9. A method of treating a disease in a patient wherein said disease is selected from melanoma or colon, ovarian, lung, stomach, or breast cancer, comprising the step of administering to said patient a therapeutically effective amount of the composition according to claim 6.

10. A method of treating an allergic disorder in a patient in need thereof, comprising the step of administering to said patient a therapeutically effective amount of the composition according to claim 6.

11. A method of treating asthma in a patient in need thereof, said method comprising administering to said patient a composition according to claim 6.

* * * * *